United States Patent
Romagne et al.

(10) Patent No.: US 9,447,185 B2
(45) Date of Patent: Sep. 20, 2016

(54) COMPOSITIONS AND METHODS FOR TREATING PROLIFERATIVE DISORDERS

(75) Inventors: Francois Romagne, La Ciotat (FR); Alessandro Moretta, Genoa (IT); Mathieu Blery, Marseilles (FR); Petrus Johannes Louis Spee, Allerod (DK); Ulrik Morch, Hellebaek (DK)

(73) Assignees: INNATE PHARMA, S.A., Marseilles (FR); UNIVERSITY OF GENOVA, Genoa (IT); NOVO NORDISK A/S, Bagsvaerd (DK)

( * ) Notice: Subject to any disclaimer, the term of this patent is extended or adjusted under 35 U.S.C. 154(b) by 903 days.

(21) Appl. No.: 12/089,314

(22) PCT Filed: Oct. 13, 2006

(86) PCT No.: PCT/EP2006/067399
§ 371 (c)(1),
(2), (4) Date: Apr. 4, 2008

(87) PCT Pub. No.: WO2007/042573
PCT Pub. Date: Apr. 19, 2007

(65) Prior Publication Data
US 2008/0274047 A1    Nov. 6, 2008

Related U.S. Application Data

(60) Provisional application No. 60/726,866, filed on Oct. 14, 2005.

(51) Int. Cl.
| | | |
|---|---|---|
| A61K 39/395 | (2006.01) | |
| A61K 39/00 | (2006.01) | |
| A61K 39/38 | (2006.01) | |
| C07K 16/28 | (2006.01) | |

(52) U.S. Cl.
CPC ........... *C07K 16/28* (2013.01); *C07K 16/2803* (2013.01); *C07K 16/2851* (2013.01); *A61K 2039/505* (2013.01)

(58) Field of Classification Search
None
See application file for complete search history.

(56) References Cited

U.S. PATENT DOCUMENTS

| | | |
|---|---|---|
| 2003/0095965 A1 | 5/2003 | Van Beneden et al. |
| 2007/0231322 A1 | 10/2007 | Romagne et al. |

FOREIGN PATENT DOCUMENTS

| | | |
|---|---|---|
| WO | 00/02583 | 1/2000 |
| WO | WO 0250122 A2 * | 6/2002 |
| WO | 2005/000086 | 1/2005 |
| WO | WO 2005/003172 A2 | 1/2005 |
| WO | WO 2005/009465 A1 | 2/2005 |
| WO | 2005/105848 | 11/2005 |
| WO | WO 2005/105849 A1 | 11/2005 |
| WO | 2010/081890 | 7/2010 |

OTHER PUBLICATIONS

Kitaichi et al., 2002, J. Leuk. biol. vol. 72: 1117-1121.*
Rogers et al., 2006, J. Immunol. vol. 177: 414-421.*
Pende et al., 1996, J. Exp. Med. vol. 184: 505-518 Kitaichi et al., 2002, J. Leuk. Biol. vol. 72: 1117-1121.*
Sola et al., 2009, PNAS. vol. 106: 12879-84 Romagne et al., 2009, Blood, vol. 114: 2667-2677.*
Perricone et al., 2008, Autoimmunity Reviews, vol. 7: 384-390
Saez-Borderias et al., 2009, J. Immunol. vol. 182: 829-836.*
Niokou et al., 2003, Human Immunol. vol. 64: 1167-1176.*
Paust et al., 2010, Immunol. Rev. 235: pp. 1-22.*
Chan et al., 2010. Nature Reviews: 301-316.*
Kodama et al., 2005. CMLS: 62:1-13.*
Kaufman et al., 2010, Exp. Derm. vol. 19: e347-e349.*
Leavenworth et al., 2011, PNAS pp. 1-6.*
Gelderman et al., Mar. 2004, TRENDS in immunology, vol. 25: 158-164.*
Xiu et al., 2008, J. Immunol. vol. 180: 2863-2875.*
Ahern et al., 2011, Immunology Letters, vol. 136: 115-121.*
Marie-Cardine et al., 2014, Canc. Res. vol. 74: 6060-70.*
Epling-Burnette, P. K. et al. "Dysregulated NK receptor expression in patients with lymphoproliferative disease of granular lymphocytes" Blood, May 1, 2004, pp. 3431-3439, vol. 103, No. 9.
European Search Report Application No. 11150593.9 dated Jul. 5, 2011.
Sivori et al., p46, Novel Natural Killer Cell-specific Surface Molecule That Mediates Cell Activation, J. Exp. Med., 1997, 186(7):1129-1136.
Walzer et al., Identification, activation, and selective in vivo ablation of mouse NK cells via NKp46, PNAS, 2007, 104(9):3384-3389.
Winkler-Pickett, R. et al. "In vivo regulation of experimental autoimmune encephalomyelitis by NK cells: alteration of primary adaptive responses," J Immunol. Apr. 1, 2008;180(7):4495-506.
Loughran TP Jr., "Clonal diseases of large granular lymphocytes," Blood. Jul. 1, 1993;82(1):1-14.

\* cited by examiner

*Primary Examiner* — Amy Juedes
(74) *Attorney, Agent, or Firm* — Robin L. Teskin; LeClairRyan, A Professional Corporation

(57) ABSTRACT

The present invention relates to methods of treating proliferative disorders, particularly immunoproliferative and autoimmune disorders, and methods of producing antibodies which bind NK cell receptors for use in therapeutic strategies for treating such disorders, particularly to deplete cells involved in the immunoproliferative pathology.

6 Claims, 3 Drawing Sheets

COMPOSITIONS AND METHODS FOR TREATING PROLIFERATIVE DISORDERS

CROSS-REFERENCE TO RELATED APPLICATION

This application is the U.S. national stage application of International Patent Application No. PCT/EP2006/067399, filed Oct. 13, 2006, which claims the benefit of U.S. Provisional Patent Application No. 60/726,866, filed Oct. 14, 2005, the disclosures of which are hereby incorporated by reference in their entireties, including all figures, tables and amino acid or nucleic acid sequences.

FIELD OF THE INVENTION

The present invention relates to methods of treating proliferative disorders, particularly immunoproliferative disorders such as NK-type LDGL, and methods of producing antibodies for use in therapeutic strategies for treating such disorders. Generally, the present methods involve the use of antibodies that specifically bind to receptors present on the surface of the proliferating cells underlying the disorders.

BACKGROUND

Natural killer (NK) cells are a sub-population of lymphocytes that are involved in non-conventional immunity. Characteristics and biological properties of NK cells include the expression of surface antigens such as CD16, CD56 and/or CD57, and the absence of the alpha/beta or gamma/delta TCR complex expressed on the cell surface; the ability to bind to and kill cells that fail to express "self" MHC/HLA antigens by the activation of specific cytolytic enzymes; the ability to kill tumor cells or other diseased cells that express a NK activating receptor-ligand; and the ability to release protein molecules called cytokines that stimulate or inhibit the immune response.

NK cell activity is regulated by a complex mechanism that involves both activating and inhibitory signals. Several distinct classes of NK-specific receptors have been identified that play an important role in the NK cell mediated recognition and killing of HLA Class I deficient target cells. One such class of receptors, the NCRs (for Natural Cytotoxicity Receptors), includes NKp30, NKp46 and NKp44, all members of the Ig superfamily. Their cross-linking, induced by specific mAbs, strongly activates NK cells, resulting in increased intracellular $Ca^{++}$ levels, triggering of cytotoxicity, and lymphokine release.

Two additional families of NK cell receptors are the KIR receptors (Killer Cell Immunoglobulin-like Receptors) and CD94/NKG2. Each of these families contain both activating and inhibitory receptors. KIR genes represent a diverse, polymorphic group of Ig superfamily members expressed on NK cells and having either two or three extracellular Ig-like domains. The cytoplasmic domains of the inhibitory members of the family, including KIR2DL1, KIR2DL2, KIR2DL3, KIR2DL5A, KIR2DL5B, KIR3DL1, KIR3DL2, and KIR3DL3, contain ITIM sequences, in contrast to the cytoplasmic domains of the activating members, such as KIR2DS1, KIR2DS2, KIR2DS3, KIR2DS4, KIR2DS5, and KIR3DS1, which usually contain a charged residue. Inhibitory members of the KIR family mediate the inhibitory effect HLA class 1 molecules. The polymorphism seen within the KIR receptor family is a result of genetic variation between individuals as well as the clonal expansion of particular NK cells in vivo. For review see, e.g., Trowsdale and Parham (2004) Eur J Immunol 34(1):7-17; Yawata et al. (2002) Crit Rev Immunol 22(5-6):463-82; Hsu et al. (2002) Immunol Rev 190:40-52; Middleton et al. (2002) Transpl Immunol 10(2-3):147-64; Vilches et al. (2002) Annu Rev Immunol 20:217-51.

CD94 and NKG2 proteins are members of the C-type lectin superfamily. CD94 is preferentially expressed on NK cells, and forms heterodimers with NKG2 family members, such as NKG2A, which is itself expressed on at least 50% of all NK cells. NKG2A contains 2 ITIM domains, and together with CD94 forms a heterodimeric inhibitory receptor that binds to nonclassical MHC class 1 molecule HLA-E (in humans; Qa-1b in mice) (see, e.g., OMIM 602894; Braud et al. (1998) Nature 391:795-799; Chang et al. (1995) Europ. J. Immun 25:2433-2437; Lazetic et al. (1996) Immun 157:4741-4745; Rodriguez et al. (1998) Immunogenetics 47:305-309.)

NK-LDGL (NK-type lymphoproliferative disease of granular lymphocytes; alternatively called NK-LGL) refers to a class of proliferative disorders that is caused by the clonal expansion of NK cells or NK-like cells, i.e., large granular lymphocytes showing a characteristic combination of surface antigen expression (e.g., CD3−, CD56+, CD16+, etc.; see, e.g., Loughran (1993) Blood 82:1). The cell proliferation underlying these disorders can have variable effects, ranging from the mild symptoms seen in some patients to the aggressive, often-fatal form of the disease called NK-LDGL leukemia. Symptoms of this class of disorders can include fever, mild neutropenia, thrombocytopenia, anemia, lymphocytosis, splenomegaly, hepatomegaly, lymphadenopathy, marrow infiltration, and others (see, e.g., Zambello et al. (2003) Blood 102:1797; Loughran (1993) Blood 82:1; Epling-Burnette et al. (2004) Blood-2003-02-400). Treatment for NK-LDGL leukemia is often aggressive, involving chemotherapy, and the disease is often fatal, associated with coagulopathy and multiple organ failure, and involving LGL infiltration of numerous organs. Autoimmune disorders are also prominent in LDGL and numerous disorders are observed including foremost rheumatoid arthritis and increased numbers of cells with a LDGL leukemic phenotype have been found in the blood or synovial fluid of rheumatoid arthritis patients. Some of these expanded cells are CD28 negative T cells having functional and phenotypical characteristics of LGL. Also observed in LDGL patients are idiopathic thrombocytopenic purpura (ITP) and aplastic anemia. Therapies useful in the treatment of NK-LDGL and LDGL generally are therefore expected to have use in the treatment of immunoproliferative and autoimmune conditions as well, particularly disorders where NK cells are implicated.

Generally, few effective therapies are effective for the treatment of established immune disorders. For example, in the case of rheumatoid arthritis, once triggered, the immune response causes inflammation of the synovium. Early and intermediate molecular mediators of inflammation include tumor necrosis factor alpha (TNF-α), interleukins IL-1, IL-6, IL-8 and IL-15, transforming growth factor beta, fibroblast growth factor and platelet-derived growth factor. Modern pharmacological treatments of RA target these mediators but do not remove the underlying cells, particularly when the cells involved are NK cells. Once the inflammatory reaction is established, the synovium thickens, the cartilage and the underlying bone begins to disintegrate and evidence of joint destruction accrues. In view of the relative dearth of effective treatments for immunoproliferative disorders, it is clear that there is a great need in the art for new and innovative strategies for limiting and reversing the immune cells activation and/or proliferation that underlies these disorders. The present invention addresses these and other needs.

SUMMARY OF THE INVENTION

To date, antibodies specific for receptors expressed on NK cells and intended to downregulate NK cell activity have generally modulated receptor function or receptor expression. That is, antibodies have blocked the functioning of activatory receptors or have activated inhibitory receptors on NK cells. Other antibodies were directed to downmodulating activatory receptors. It has now been demonstrated that antibodies directed to receptors expressed on NK cells can be used to deplete (kill) NK cells expressing the receptor of interest. Moreover, this NK cell depletion can be mediated by "naked" antibodies which are not functionalized with toxic moieties. Antibodies having effector regions which bind Fc receptors, and particularly CD16 are particularly preferred.

The inventors have also demonstrated that these depleting antibodies can eliminate cells in vivo, in all organs tested and in bone marrow. This is an important feature because it indicates that the antibodies can be used to treat immunoproliferative disorders involving NK cells located within organs (and not only circulating NK cells), and because it indicates that the depleting antibodies can be used to treat an established immunoproliferative condition, e.g. where autoreactive NK cells have already emerged and have become involved in the pathology. Because immunoproliferative disorders are often diagnosed once they are well established, depleting NK cells rather than inhibiting their activity or preventing further proliferation is important.

The present invention provides antibodies, and methods for producing antibodies, useful for the treatment of proliferative disorders, particularly immunoproliferative disorders such as NK-type LDGL and other disorders believed to involve NK cells. NK cells have been reported to be involved in immunoproliferative disorders such as rheumatoid arthritis and diabetes for example. Thus the antibodies of the invention are expected to be useful in the treatment of for example asthma, arthritis, including osteoarthritis, rheumatoid arthritis, and spondyloarthropathies, gastrointestinal inflammation, Crohn's disease and ulcerative colitis, neuroinflammatory disorders, and autoimmune disorders such as type I diabetes, rheumatoid arthritis, systemic lupus erythematosus, dermatomyositis, psoriasis, Sjogren's syndrome, lupus erythematosus, demyelinating conditions, multiple sclerosis, myasthenia gravis, Reiter's syndrome, Grave's disease, polymyositis, Guillain Barré, Wegener's granulomatosus, polyarteritis nodosa, polymyalgia rheumatica, temporal arteritis, Bechet's disease, Churg-Strauss syndrome, Takayasu's arteritis, and others. In one embodiment, the immunoproliferative disorders specifically excludes NK-type LDGL and T-LDGL. The antibodies produced using the present methods are capable of specifically targeting the expanded cells underlying such disorders, such as expanded NK cells in NK-type LDGL or expanded T or NK cells in immunoproliferative and particularly autoimmune disorders such as rheumatoid arthritis and type I diabetes. The antibodies can limit the pathological effects of the cell proliferation by, e.g., by targeting them for destruction by the immune system, or, by killing the cells directly by contacting them with a cytotoxic agent such as a radioisotope, toxin, or drug. Methods of using the antibodies for the treatment of any of a number of proliferative disorders are also provided, as are kits comprising the herein-described antibodies as well as instructions for their use.

Accordingly, the present invention provides a method of treating a patient with an immunoproliferative disorder involving NK cells, the method comprising administering an antibody to the patient that specifically binds to an NK receptor. Also encompassed is a method of reducing inflammation in an individual, or a method of eliminating, killing or depleting NK or T cells in an individual.

In another embodiment, the invention provides the use of a composition comprising an antibody that specifically binds to a NK receptor and which when bound to said NK receptor on a human NK cell causes said NK cell to be depleted, for the manufacture of a medicament for the treatment of an immunoproliferative disorder.

In another aspect, the invention provides a method of eliminating an NK cell, a method for eliminating an activated NK cell, a method for decreasing inflammation, or a method for decreasing proinflammatory cytokines in an individual or in a biological sample, the method comprising contacting said NK cell with a composition comprising an antibody that specifically binds to a NK receptor.

In another aspect the invention provides a method for depleting NK and/or T cells in a mammal, the method comprising administering to the mammal a composition comprising an antibody that specifically binds to a NK receptor.

In another aspect, the invention provides a method for reducing inflammation, decreasing numbers of activated NK cells, or decreasing proinflammatory cytokines in a mammal or in a biological sample, the method comprising the method comprising eliminating NK cells that express NKG2A and/ or cells that express NKG2C. Preferably NK cells that express NKG2A and cells that express NKG2C are eliminated. Preferably, eliminating NK or T cells comprises bringing said NK cells into contact with a composition comprising an antibody that specifically binds to NKG2A and/or NKG2C.

In one example, said step of bringing into contact takes place in a cell culture medium comprising cellular effectors, optionally said culture medium comprises PBMC or total peripheral blood lymphocytes. In another aspect, said step of bringing into contact takes place in vivo in a mammal.

In another aspect, the invention provides a method for treating an individual comprising: a) diagnosing the presence of immunoproliferative disorder (e.g. symptoms and/or presence of NK cells and/or cells expressing an NK cell receptor, b) treating with antibody of the invention. In one aspect, the step of diagnosing comprises diagnosing an established inflammatory or autoimmune disorder, optionally wherein an established disorder is characterized by tissue damage or injury or symptoms thereof and/or a disorder that persists for more than 3, 6, 9, 12, 24 or 36 months.

The present invention also provides a method of treating a patient with an immunoproliferative disorder, the method comprising a) determining the NK receptor status of NK cells within the patient, and b) administering an antibody to the patient that specifically binds to an NK receptor that is prominently expressed in the NK cells.

In one embodiment of the methods of the invention, the NK receptor is an activating receptor. In another embodiment, the receptor is selected from the group consisting of KIR2DL1, KIR2DS1, KIR2DL2, KIR2DL3, KIR2DS4, NKG2C, NKG2D, NKG2E, NKG2F, CD94, and NKG2A. In another embodiment, the receptor is an NCR such as NKp30, NKp44, or NKp46. In another embodiment, the antibody specifically binds to a single NK receptor. In another embodiment, the NK receptor status is determined using an immunological assay. In another embodiment, the NK receptor status is determined using a functional assay to determine the activity of the NK receptors present on the NK cells. In another embodiment, the NK receptor status is determined using a genotyping assay. In another embodiment, the NK receptor status is determined using an assay to detect NK receptor-encoding mRNA in the cells. In another embodiment, the receptor is detectably present on at least 50% of the NK cells.

In another embodiment, the antibody is a cytotoxic antibody. In another aspect the antibodies kill cells expressing the receptor or receptors, for example by mediating ADCC (antibody dependent cytotoxicity) or CDC (complement-dependent cytotoxicity) toward the cells (e.g. antibodies of the human IgG1 or IgG3 type).

In a preferred embodiment, the antibody is a "naked" antibody capable of recruiting cellular effectors. The function of the monoclonal naked antibodies and fragments thereof of this invention will generally be dependent upon their ability to bind to an Fc receptor. Fc receptors, such as Fc gamma receptors, are expressed on the surface of leukocytes. These receptors bind to the Fc portion of immunoglobulin (Ig), e.g. Fc gamma receptors bind to the Fc portion of IgG. This binding helps contribute to immune function by linking the recognition of antigens by antibodies with cell-based effector mechanisms. Different immunoglobulin classes trigger different effector mechanisms through the differential interaction of immunoglobulin Fc regions with specific Fc receptors (FcRs) on immune cells. Activating Fc gamma receptors include Fc gamma RI, Fc gamma RIIA, Fcgamma RIIC, and Fcgamma RIII A. Fc gamma RIIB is considered an inhibitory Fc gamma receptors. (For review, see, e.g., Woof et al. (2004) Nat Rev Immunol. 4(2):89-99; Baumann et al. (2003) Arch Immunol Ther Exp (Warsz) 51(6):399-406; Pan et al. (2003) Chin Med J (Engl) 116(4):487-94; Takai et al. (1994) Cell 76:519-529; Ravetch et al. (2001) Annu Rev Immunol 19:275-290, the entire disclosures of each of which in herein incorporated by reference). Without being bound by theory, the inventors believe that the presence of an Fc receptor binding region in the antibodies of this invention leads to depletion of the cells to which the antibodies of the invention are bound. In a preferred aspect the antibody comprises a human Fc region of the IgG1 or IgG3 type and does not contain a toxic or radioactive moiety. In another embodiment, the Fc region is a human IgG2 or IgG4 which binds a human Fc receptor and optionally modified to confer or increase binding to a human Fc receptor.

In another embodiment, the cytotoxic antibody comprises an element selected from the group consisting of radioactive isotope, toxic peptide, and toxic small molecule. In another embodiment, the antibody is an antibody fragment. In another embodiment, the antibody is humanized or chimeric. In another embodiment, the radioactive isotope, toxic peptide, or toxic small molecule is directly attached to the antibody. In another embodiment, the antibody binds to a mouse or primate homolog of said NK receptor. In another embodiment, the antibody binds to a plurality of KIR receptors. In another embodiment, the cytotoxic antibody is derived from the same antibody used to determine said NK receptor status in the immunological assay.

In another aspect, the present invention provides a method of producing an antibody suitable for use in the treatment of an immunoproliferative disorder, said method comprising: i) providing a plurality of antibodies that specifically bind to one or more NK cell receptors; ii) testing the ability of each of the antibodies to bind to NK cells taken from one or more patients with the immunoproliferative disorder; iii) selecting an antibody from the plurality that binds to at least 50% of the NK cells taken from one or more of the patients; and iv) making the antibody suitable for human administration.

In one embodiment, the antibody specifically binds to an activating NK cell receptor. In another embodiment, the antibody specifically binds to a receptor selected from the group consisting of KIR2DL1, KIR2DS1, KIR2DL2, KIR2DL3, KIR2DS4, CD94, NKG2D, NKG2E, NKG2F, NKG2C and NKG2A. In another embodiment, the antibody specifically binds to an NCR such as NKp30, NKp44, or NKp46. In another embodiment, the antibody is made suitable for human administration by humanizing or chimerizing it.

In another embodiment, the method further comprises the step of linking a cytotoxic agent to the antibody. In another embodiment, the cytotoxic agent is a radioactive isotope, a toxic polypeptide, or a toxic small molecule. In another embodiment, the cytotoxic agent is directly linked to the antibody. In another embodiment, the antibody is an antibody fragment. In another embodiment, the antibody binds to at least 60% of the NK cells taken from one or more of the patients. In another embodiment, the antibody binds to at least 70% of the NK cells taken from one or more of the patients. In another embodiment, the antibody binds to at least 80% of the NK cells taken from one or more of the patients.

In another aspect the invention provides a method of treating a patient with an immunoproliferative disorder, the method comprising a) determining the NK cell receptor status of T cells or NK cells within said patient, and b) administering an antibody to said patient that specifically binds to a NK cell receptor that is prominently expressed by said T cells or NK cells, wherein the wherein said receptor is selected from the group consisting of KIR2DL1, KIR2DS1, KIR2DL2, KIR2DL3, KIR2DS4, CD94, NKG2A, NKG2C, NKG2D, NKG2E, NKG2F, NKp30, NKp44, and NKp46. The invention also provides a method of treating a patient with an immunoproliferative disorder, the method comprising a) determining the NK receptor status of T cells or NK cells within said patient, and b) eliminating NK or T cells from the patient by bringing NK or T cells from the patient into contact with a composition comprising an antibody to said patient that specifically binds to a NK receptor that is prominently expressed by said T cells or NK cells, wherein the antibody causes said T or NK cell to which it bound to be depleted.

In another aspect the invention provides a method of treating a patient having an immunoproliferative disorder, or a method of reducing inflammation in an individual, or a method of eliminating, killing or depleting NK or T cells in an individual, the method comprising administering an antibody to the patient that specifically binds to a NK cell receptor selected from the group consisting of KIR2DL1, KIR2DS1, KIR2DL2, KIR2DL3, KIR2DS4, CD94, NKG2A, NKG2C, NKG2D, NKG2E, NKG2F, NKp30, NKp44, and NKp46.

In one embodiment of the methods of the invention, the NK receptor is an activating receptor. In another embodiment, the receptor is selected from the group consisting of KIR2DL1, KIR2DS1, KIR2DL2, KIR2DL3, KIR2DS4, and CD94. In another embodiment, the receptor is an NCR such as NKp30, NKp44, or NKp46. In another embodiment the receptor is an inhibitory receptor, preferably a NKG2 protein such as NKG2D, NKG2E, NKG2F, NKG2C and NKG2A.

In another embodiment, the antibody specifically binds to a single NK cell receptor. In another embodiment, the NK receptor status is determined using an immunological assay. In another embodiment, the NK receptor status is determined using a functional assay to determine the activity of the NK receptors present on the T or NK (or other) cells. In another embodiment, the NK receptor status is determined using a genotyping assay. In another embodiment, the NK receptor status is determined using an assay to detect NK receptor-encoding mRNA in the cells. In another embodiment, the receptor is detectably present on at least 50% of the particular set of T cells or NK (or other) cells.

In another embodiment, the antibody is an antibody fragment. Preferably, the antibody is a cytotoxic antibody and the antibodies lead to the killing of cells expressing the receptor or receptors, for example by mediating ADCC toward the cells (e.g. antibodies of the IgG1 or IgG3 type). In another embodiment, the cytotoxic antibody comprises an element selected from the group consisting of radioactive isotope, toxic peptide, and toxic small molecule. In one aspect, the antibodies additionally block receptor function such as ligand binding or signalling and/or cause receptor internalization. In another embodiment, the antibody is humanized or chimeric. In another embodiment, the radioactive isotope, toxic peptide, or toxic small molecule is directly attached to the antibody. In another embodiment, the antibody binds to a mouse or primate homolog of said T or NK receptor. In another embodiment, the antibody binds to a plurality of KIR receptors. In another embodiment, the cytotoxic antibody is derived from the same antibody used to determine said T or NK receptor status in the immunological assay.

In another aspect, the present invention provides a method of producing an antibody suitable for use in the treatment of an immunoproliferative disorder, said method comprising: i) providing a plurality of antibodies that specifically bind to one or more NK receptors; ii) testing the ability of each of the antibodies to bind to NK or T cells taken from one or more patients with an immunoproliferative disorder; iii) selecting an antibody from the plurality that binds to at least 50% of the NK or T cells taken from one or more of the patients; and iv) making the antibody suitable for human administration.

In one embodiment, the antibody specifically binds to an activating receptor. In another embodiment, the antibody specifically binds to a receptor selected from the group consisting of KIR2DL1, KIR2DS1, KIR2DL2, KIR2DL3, KIR2DS4, CD94, NKG2D, NKG2E, NKG2F, NKG2C and NKG2A. In another embodiment, the antibody specifically binds to an NCR such as NKp30, NKp44, or NKp46, NKG2C or NKG2D. In another embodiment, the antibody is made suitable for human administration by humanizing or chimerizing it. In another embodiment, the method further comprises the step of linking a cytotoxic agent to the antibody. In another embodiment, the cytotoxic agent is a radioactive isotope, a toxic polypeptide, or a toxic small molecule. In another embodiment, the cytotoxic agent is directly linked to the antibody. In another embodiment, the antibody is an antibody fragment. In another embodiment, the antibody binds to at least 60% of the NK or T cells taken from one or more of the patients. In another embodiment, the antibody binds to at least 70% of the NK or T cells taken from one or more of the patients. In another embodiment, the antibody binds to at least 80% of the NK or T cells taken from one or more of the patients.

In another aspect, the monoclonal antibody of the invention is characterized by:

specifically binding to an NK cell receptor selected from the group consisting of human KIR2DL1, KIR2DS1, KIR2DL2, KIR2DL3, KIR2DS4, CD94, NKG2A, NKG2C, NKG2D, NKG2E, NKG2F, NKp30, NKp44, and NKp46;

binding to an $F_c$ receptor; and when bound to said NK cell receptor on a human NK cell, causes said NK cell to be depleted. Preferably said antibody is humanized or chimeric.

Preferably said antibody specifically binds NKp46, NKG2A or NKG2C. Optionally said antibody specifically binds NKG2A and NKG2C, or optionally said antibody specifically binds NKG2A, NKGC and NKG2E. In one example said antibody competes with Z199 or Z270 for binding to NKG2A and/or comprises a complementarity-determining region from NKG2A. Preferably said antibody comprises an Fc region of the G1 or G3 isotype.

In certain aspects of the any of the embodiments herein, the immunoproliferative disorder is an autoimmune disorder selected from the group consisting of allergies, asthma, arthritis, including osteoarthritis, rheumatoid arthritis, and spondyloarthropathies, gastrointestinal inflammation, Crohn's disease and ulcerative colitis, neuroinflammatory disorders, Hashimoto's thyroiditis, pernicious anemia, Addison's disease, type I diabetes, rheumatoid arthritis, systemic lupus erythematosus, dermatomyositis, psoriasis, Sjogren's syndrome, lupus erythematosus, demyelinating conditions, multiple sclerosis, myasthenia gravis, Reiter's syndrome, Grave's disease, polymyositis, Guillain Barré, Wegener's granulomatosus, celiac disease, polyarthritis nodosa, polymyalgia rheumatica, temporal arteritis, Bechet's disease, Churg-Strauss syndrome and Takayasu's arteritis. Preferably the immunoproliferative disorder is NK-LDGL or T-LDGL, rheumatoid arthritis, type I diabetes or a disorder selected from the group consisting of: ITP, multiple sclerosis, Wegener's granulomatosis, and Sjogren's syndrome. In certain aspects of the methods for treating an immunoproliferative disorder, the said cell is a T cell. In one embodiment the T cell is $CD3^+$ and optionally $CD4^+CD28^-$ or $CD8^+$, these cells also having been reported to express NK cell receptors. In exemplary aspects the antibody binds NKG2A and binds substantially the same epitope as an antibody selected from the group consisting of Z199 and Z270. In another exemplary aspects the antibody binds NKp46 and binds substantially the same epitope as an antibody selected from the group consisting of BAT281. In another exemplary aspect the antibody binds KIR2DL1, KIR2DL2 and/or KIR2DL3 and binds substantially the same epitope as an antibody DF200, NKVSF or 1-7F9 described in PCT patent publication nos WO 2005/003172 and WO 06/003179, the disclosure of which are incorporated herein by reference. and binds substantially the same epitope as an antibody selected from the group consisting of Z199 and Z270. In exemplary aspects the antibody binds NKG2D and binds substantially the same epitope as an antibody selected from the group consisting of BAT221, ECM217, and ON72.

In another aspect of any of the embodiments described herein, the immunoproliferative disease, including the inflammatory or autoimmune disorder, is an established disease. Preferably the disease is characterized by physical symptoms, (e.g. tissue injury, destruction, swelling, etc.), according to medical criteria (e.g. ACR), mediated by immune cells and/or does not subside over a defined period of time (e.g. 3, 6, 9, 12, 24, or 36 months).

In other aspects of any of the embodiments described herein, the present invention provides antibodies produced using any of the herein-described methods. The invention also encompasses fragments and derivatives of the antibodies having substantially the same antigen specificity and activity (e.g., which can bind to the same antigens as the parent antibody). Such fragments include, without limitation, Fab fragments, Fab'2 fragments, CDR and ScFv.

In other aspects, the present invention provides kits comprising any one or more of the herein-described antibodies. One embodiment, the kit comprises at least one diagnostic antibody and at least one therapeutic (e.g., cytotoxic) antibody. In another embodiment, the diagnostic antibody and the therapeutic antibody specifically bind to the same NK cell receptor. In another embodiment, the kit also comprises instructions for using the antibodies according to the present methods.

The invention also comprises pharmaceutical compositions comprising one or more of the present antibodies, or a fragment or derivative thereof, and a pharmaceutically acceptable carrier or excipient.

DETAILED DESCRIPTION OF THE INVENTION

Introduction

Figure 1A:
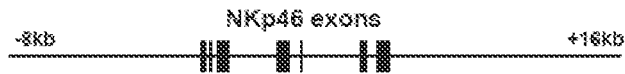
FIG. 1. Human NKP46 genomic sequence can be used to genetically tag mouse NK cells: (a) Schematic representation of the human genomic fragment used for transgenesis. NKP46 exons are shown as black bars. (b) Spleen cell suspensions obtained from huNKp46 transgenic mice were stained for NK1.1, human NKp46 and other cell surface molecules expression. The indicated cell types were identified as described in the experimental procedures. (c) Bone marrow cells from huNKp46 transgenic mice were stained for CD3, CD122, DX5, NK1.1 and human NKp46 expression. NK precursors (NKp), immature and mature NK cells were identified. (d) Lymph node (inguinal), liver, lung and peripheral blood cell suspensions obtained from huNKp46 transgenic mice were stained for CD3, NK1.1 and human NKp46 expression. Results in (b-d) show the expression of human NKp46 (open histogram, thick line) or isotype control (grey histogram, thin line) in the indicated subsets or in gated CD3-NK1.1+ cells (c). (e) Redirected lysis assay of LAK cells derived from B6 (C57BL/6) or huNKp46 Tg (Tg) spleen cells against Daudi cells incubated with the indicated antibodies. The cytolytic function of LAK cells prepared from B6 and huNKp46 Tg mice were comparable. Results in FIG. 1 are representative of 3 experiments.

The present invention provides novel methods for producing and using antibodies suitable for the treatment of proliferative, particularly immunoproliferative, disorders such as NK-type lymphoproliferative disease of granular lymphocytes (NK-LDGL). Antibodies, antibody derivatives, or antibody fragments produced using the herein described methods are encompassed, as are methods of treating patients using the antibodies. In particular, the present methods involve typing the proliferating NK- or NK-like cells underlying these disorders in order to determine which one or more NK cell receptors is prominently displayed on the proliferating cells, and then treating the patient using antibodies that specifically bind to the same receptor or receptors.

NK-LDGL and other immunoproliferative disorders are often characterized by the clonal expansion of one or a small number of NK or NK-like cells. Accordingly, because individual NK cells generally express only a subset of NK cell receptors, a substantial portion of the overproliferating cells underlying these disorders often express a small number of NK cell receptors. The present invention thus provides a method of treating these disorders by identifying the particular receptor or receptors that are expressed in the proliferating cells in a given patient, and then specifically targeting those cells that express the receptor or receptors using cytotoxic antibodies. In this way, the number of overproliferating cells is specifically reduced, while sparing other immune and non-immune cells.

Generally, the present methods involve the use of a panel of monoclonal antibodies that are each specific for one or a small number NK cell receptors, such as KIR receptors, CD94, one of the NKG2 receptors, or an NCR such as NKp30, NKp44, NKp46. Often, two sets of antibodies are used. One set, comprising directly or indirectly labeled antibodies, are diagnostic in nature and used to determine which particular NK cell receptor or receptors is expressed on the NK cells from a given patient. The second set, used for treatment, corresponds to monoclonal antibodies that are generally raised in a non-human animal but which have been rendered suitable for use in humans, e.g., are humanized or chimerized. In one aspect, the antibodies block receptor function such as ligand binding or signalling and/or cause receptor internalization. In another aspect the antibodies kill cells expressing the receptor or receptors, for example by mediating ADCC toward the cells (e.g. antibodies of the IgG1 or IgG3 type). In certain embodiments, the antibodies are further derivatized with cytotoxic agents, directly or indirectly, so that they kill cells expressing the receptor or receptors. For example, the antibodies can be linked to radioactive isotopes, cytotoxic polypeptides, or cytotoxic small molecules.

DEFINITIONS

As used herein, the following terms have the meanings ascribed to them unless specified otherwise.

As used herein, "NK" cell refers to a sub-population of lymphocytes that are involved in non-conventional immunity. NK cells can be identified by virtue of certain characteristics and biological properties, such as the expression of specific surface antigens including CD16, CD56 and/or CD57, the absence of the alpha/beta or gamma/delta TCR complex on the cell surface, the ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art.

The term "NK cell receptor" refers to any cell surface molecule that is found consistently on all or a fraction of NK cells. Preferably, the NK cell receptor is expressed exclusively on NK cells (resting or activated), although the term also encompasses receptors that are also expressed on other cell types. Examples of NK cell receptors include members of the KIR receptor family, CD94, NKG2 receptors, NCR receptors such as NKp30, NKp44, and NKp46, LIR-1, and others (see, e.g., Trowsdale and Parham (2004) Eur J Immunol 34(1):7-17; Yawata et al. (2002) Crit Rev Immunol 22(5-6):463-82; Hsu et al. (2002) Immunol Rev 190:40-52; Middleton et al. (2002) Transpl Immunol 10(2-3):147-64; Vilches et al. (2002) Annu Rev Immunol 20:217-51; OMIM 602894; Braud et al. (1998) Nature 391:795-799; Chang et al. (1995) Europ. J. Immun 25:2433-2437; Lazetic et al. (1996) Immun 157:4741-4745; Rodriguez et al. (1998) Immunogenetics 47:305-309; OMIM 161555; Houchins et al. (1991) J. Exp. Med. 173:1017-1020; Adamkiewicz et al. (1994) Immunogenetics 39:218; Renedo et al. (1997) Immunogenetics 46:307-311; Ravetch et al. (2000) Science 290: 84-89; PCT WO 01/36630; Vitale et al. (1998) J. Exp. Med. 187:2065-2072; Sivori et al. (1997) J. Exp. Med. 186:1129-1136; Pessino et al. (1998) J. Exp. Med. 188:953-960; the disclosures of each of which is herein incorporated by reference).

As used here, "NK receptor status" refers to the identity and prominence of the various NK cell receptors expressed on NK or other cells taken from an individual, e.g., a patient having an immunoproliferative disorder. For example, an examination of NK cells taken from a patient may find that a particular NK cell receptor, e.g., KIR2DS2, is expressed in 70% of the cells, that another receptor, e.g., KIR2DL1, is expressed in 40% of the cells, that another receptor, e.g., CD94, is expressed on 80% of the cells, etc. Such information is useful for determining which cytotoxic antibodies to use in the present methods. It will be appreciated that, while it is clearly useful to have expression information concerning multiple NK cell receptors, NK receptor status can also refer to the expression level or prominence of a single receptor, e.g., KIR2DS2, or small number of receptors, e.g., KIR2DL2/3 and KIR2DS2.

"LGL," or "large granular lymphocytes," refers to a morphologically distinct population of lymphoid cells. LGL, which make up 10-15% of the peripheral blood mononuclear cells. LGLs can include both NK cells and T cells (see, e.g., Loughran (1993) Blood 82:1-14), which can be distinguished by virtue of certain markers, e.g. CD3 expression (with NK cells being CD3$^-$ and T cells CD3$^+$). Preferably, for the purposes of the present invention, the LGL cells are CD3$^-$. In certain embodiments of the present invention, however, PBLs will be taken from a patient, and examined to see if any cell type is expanded, preferably LGLs, most particularly CD3$^-$ LGLs. In general, any expanded cell type can be examined to determine whether particular NK cell receptors are prominently expressed on their surface.

"Prominently expressed" refers to an NK cell receptor that is expressed in a substantial number of cells of a specified type (e.g., NK cells, T cells) taken from a given patient. While the definition of the term "prominently expressed" is not bound by a precise percentage value, in most cases a receptor said to be "prominently expressed" will be present on at least 30%, 40%, preferably 50°%, 60%, 70%, 80%, or more of the NK cells, T cells or other overproliferating cells taken from a patient.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu" respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. Preferably the antibody of this invention is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. an NK cell receptor such as an activating KIR receptor, as assessed using either recombinant forms of the proteins, epitopes therein, or native proteins present on the surface of isolated NK or relevant target cells. Competitive binding assays and other methods for determining specific binding are further described below and are well known in the art.

The term "deplete" or "depleting" in the context of the effect of a antibody recognizing an NK cell receptor (e.g. NKG2A, NKp46), refers to a reduction or elimination of the NK receptor-expressing cells (e.g. cells that express NKG2A or NKp46).

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

"Toxic" or "cytotoxic" peptides or small molecules encompass any compound that can slow down, halt, or reverse the proliferation of cells, decrease their activity (e.g., the cytolytic activity of NK cells) in any detectable way, or directly or indirectly kill them. Preferably, toxic or cytotoxic compounds work by directly killing the cells, by provoking apoptosis or otherwise. As used herein, a toxic "peptide" can include any peptide, polypeptide, or derivative of such, including peptide- or polypeptide-derivatives with unnatural amino acids or modified linkages. A toxic "small molecule" can includes any toxic compound or element, preferably with a size of less than 10 kD, 5 kD, 1 kD, 750 D, 600 D, 500 D, 400 D, 300 D, or smaller.

By "immunogenic fragment", it is herein meant any polypeptidic or peptidic fragment which is capable of eliciting an immune response such as (i) the generation of antibodies binding said fragment and/or binding any form of the molecule comprising said fragment, including the membrane-bound receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammalian immunoglobulins. Alternatively, an immunogenic fragment also refers to any construction capable of eliciting an immune response as defined above, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

For the purposes of the present invention, a "humanized" antibody refers to an antibody in which the constant and variable framework region of one or more human immunoglobulins is fused with the binding region, e.g. the CDR, of an animal immunoglobulin. Such humanized antibodies are designed to maintain the binding specificity of the non-human antibody from which the binding regions are derived, but to avoid an immune reaction against the non-human antibody.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "human" antibody is an antibody obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

Within the context of this invention, "active" or "activated" NK cells designate biologically active NK cells, more particularly NK cells having the capacity of lysing target cells. For instance, an "active" NK cell is able to kill cells that express an NK activating receptor-ligand and fails to express "self" MHC/HLA antigens (KIR-incompatible cells). Examples of suitable target cells for use in redirected killing assays are P815 and K562 cells, but any of a number of cell types can be used and are well known in the art (see, e.g., Sivori et al. (1997) J. Exp. Med. 186: 1129-1136; Vitale et al. (1998) J. Exp. Med. 187: 2065-2072; Pessino et al. (1998) J. Exp. Med. 188: 953-960; Neri et al. (2001) Clin. Diag. Lab. Immun. 8:1131-1135). "Active" or "activated" cells can also be identified by any other property or activity known in the art as associated with NK activity, such as cytokine (e.g. IFN-γ and TNF-α) production of increases in free intracellular calcium levels.

As used herein, the term NK-LDGL refers to any proliferative disorder characterized by clonal expansion of NK cells or NK-like cells, e.g., large granular lymphocytes with a characteristic set of surface antigens (e.g., CD3−, CD56+, CD16+), (see, e.g., Zambello et al. (2003) Blood 102:1797; Loughran (1993) Blood 82:1; Epling-Burnette et al. (2004) Blood-2003-02-400), or expressing any NK cell receptor, as defined herein. Symptoms of NK-LDGL can include, inter alia, fever, mild neutropenia, thrombocytopenia, anemia, lymphocytosis, splenomegaly, hepatomegaly, lymphadenopathy, and marrow infiltration (see, e.g., Zambello et al. (2003) Blood 102:1797; Loughran (1993) Blood 82:1; Epling-Burnette et al. (2004) Blood-2003-02-400).

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The term "biological sample" as used herein includes but is not limited to a biological fluid (for example serum, lymph, blood), cell sample or tissue sample (for example bone marrow).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Producing Monoclonal Antibodies Specific for NK Cell Receptors

The present invention involves the production and use of antibodies, antibody fragments, or antibody derivatives that are suitable for use in humans and that target one or a small number of NK cell receptors. The antibodies of this invention may be produced by any of a variety of techniques known in the art. Typically, they are produced by immunization of a non-human animal, preferably a mouse, with an immunogen comprising a receptor present on the surface of NK cells. The receptor may comprise entire NK cells or cell membranes, the full length sequence of an NK cell receptor, or a fragment or derivative of any NK cell receptor, typically an immunogenic fragment, i.e., a portion of the polypeptide comprising an epitope exposed on the surface of cells expressing the receptor. Such fragments typically contain at least 7 consecutive amino acids of the mature polypeptide sequence, even more preferably at least 10 consecutive amino acids thereof. They are essentially derived from the extracellular domain of the receptor. It will be appreciated that any receptor any other receptor that is sometimes or always present on the surface of all or a fraction of NK cells, in some or all patients, can be used for the generation of antibodies. In preferred embodiments, the activating NK cell receptor used to generate antibodies is a human receptor.

In a most preferred embodiment, the immunogen comprises a wild-type human NK receptor polypeptide in a lipid membrane, typically at the surface of a cell. In a specific embodiment, the immunogen comprises intact NK cells, particularly intact human NK cells, optionally treated or lysed. The antibodies can be prepared against any protein or molecule present on the surface of NK cells, preferably an NK cell receptor, more preferably an NK cell receptor selected from the group consisting of KIR receptors, LIR receptors such as LIR-1, Ly49, CD94/NKG2A, NCRs such as NKp30, NKp44, and NKp46, and most preferably an activating NK cell receptor such as KIR2DS1, KIR2DS2, KIR2DS3, KIR2DS4, KIR2DS5, and KIR3DS1 (see, e.g., Trowsdale and Parham (2004) Eur J Immunol 34(1):7-17; Yawata et al. (2002) Crit Rev Immunol 22(5-6):463-82; Hsu et al. (2002) Immunol Rev 190:40-52; Middleton et al. (2002) Transpl Immunol 10(2-3):147-64; Vilches et al. (2002) Annu Rev Immunol 20:217-51; the entire disclosures of each of which is herein incorporated by reference); or NKG2D, an activating cell surface molecule that is found consistently on all or a fraction of numerous types of immune cells, particularly NK cells, CD8$^+$ T cells, some CD4$^+$ T cells, and gamma/delta T cells. NKG2D is also referred to as killer cell lectin-like receptor, subfamily C, member 4, or as KLRC4 (see, e.g., OMIM 602893, the entire disclosure of which is herein incorporated by reference in its entirety.) As used herein NKG2D refers to any NKG2D isoform, e.g., the isoforms described in Diefenbach et al. (2002) Nat Immunol. 3(12):1142-9). In NK and T cells, NKG2D can form heterodimers with proteins such as DAP10 (see, e.g., OMIM 604089) or DAP12 (see, e.g., OMIM 604142). It will be appreciated that any activity attributed herein to NKG2D, e.g., cell activation, recognition by antibodies, etc., can also refer to NKG2D-including complexes such as NKG2D-DAP10 or NKG2D-DAP12 heterodimers.

In one embodiment, the antibodies are derived from one or more already-existing monoclonal antibodies that recognize one or more NK cell receptors. Examples of suitable antibodies are as follows.

A first preferred example is an antibody recognizing NKG2A, such as antibodies referred to as 3S9, 20d5, Z270 or Z199, or derivatives thereof. 3S9 is described in United States patent publication 20030095965, the disclosure of which is herein incorporated by reference. 3S9 binds to NKG2C and NKG2E, as well as to NKG2A. 20d5 is a commercially available antibody (BD Biosciences Pharmingen, Catalog No. 550518, USA). 20d5 binds to mouse NKG2A, NKG2E and NKG2C. Z199 is a commercially available antibody (Beckman Coulter, Inc., Product No. IM2750, USA). Z270 is described in copending PCT patent publication no. WO 06/070286, the disclosure of which is incorporated herein by reference in its entirety. Z270 was deposited on Dec. 22, 2005 at the Collection Nationale de Culture de Microorganismes (CNCM), Institute Pasteur, 25, Rue du Docteur Roux, F-75725 Paris, France, under accession number I-3549. Z270 binds specifically to human NKG2A, but not to human NKG2C or NKG2E. In other embodiments, the antibody of the invention specifically excludes Z270.

Other preferred examples include EB6b (recognizing KIR2DL1, KIR2DS1), GL183 (KIR2DL2/3, KIR2DS2), FES172 (KIR2DS4), Z27 (KIR3DL1, KIR3DS1), Q66 (KIR3DL2), XA185 (CD94), Z199 (NKG2A), F278 (LIR-1), BAB281 (NKp46), AZ20 deposited as CNCM registration no. 1-2576 (NKp30), Z231 (NKp44) or 1D11, BAT221, ECM217, and ON72 (NKG2D). See, e.g., Zambello et al. (2003) Blood 102:1797-1805; Groh et al. (2003) PNAS 100:9452-57; André et al. (2004) Eur. J. Immunol. 34:1-11, the entire disclosure of the foregoing three references incorporated by reference. Such antibodies can be directly or indirectly labeled (i.e., used with a labeled secondary antibody) for use as diagnostic antibodies for the herein-described typing step to determine the NK receptor status of patients. In addition, the antibodies can be made suitable for human administration and, optionally, made toxic as described herein for use as cytotoxic antibodies in the present therapeutic methods.

The present diagnostic or therapeutic (e.g. cytotoxic) antibodies can be full length antibodies or antibody fragments or derivatives. Examples of antibody fragments include Fab, Fab', Fab'-SH, F(ab')$_2$, and Fv fragments; diabodies; single-chain Fv (scFv) molecules; single chain polypeptides containing only one light chain variable domain, or a fragment thereof that contains the three CDRs of the light chain variable domain, without an associated heavy chain moiety; single chain polypeptides containing only one heavy chain variable region, or a fragment thereof containing the three CDRs of the heavy chain variable region, without an associated light chain moiety; and multispecific antibodies formed from antibody fragments. Such fragments and derivatives and methods of preparing them are well known in the art. For example, pepsin can be used to digest an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993)). While various antibody fragments are defined in terms of the digestion of an intact antibody, one of skill will appreciate that such fragments may be synthesized de novo either chemically or by using recombinant DNA methodology.

The preparation of monoclonal or polyclonal antibodies is well known in the art, and any of a large number of available techniques can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to desired polypeptides, e.g., NK cell receptors such as KIR2DS1, KIR2DS2, KIR2DS3, KIR2DS4, KIR2DS5, and KIR3DS1. Also, transgenic mice, or other organisms such as other mammals, may be used to express humanized, chimeric, or similarly-modified antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). In one embodiment, the method comprises selecting, from a library or repertoire, a monoclonal antibody or a fragment or derivative thereof that cross reacts with at least one NK receptor. For example, the repertoire may be any (recombinant) repertoire of antibodies or fragments thereof, optionally displayed by any suitable structure (e.g., phage, bacteria, synthetic complex, etc.).

The step of immunizing a non-human mammal with an antigen may be carried out in any manner well known in the art for (see, for example, E. Harlow and D. Lane, *Antibodies: A Laboratory Manual.*, Cold Spring Harbor Laboratory Press, Cold Spring Harbor, N.Y. (1988)). Generally, the immunogen is suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

In another embodiment, lymphocytes from an unimmunized non-human mammal are isolated, grown in vitro, and then exposed to the immunogen in cell culture. The lymphocytes are then harvested and the fusion step described below is carried out.

For monoclonal antibodies, which are preferred for the purposes of the present invention, the next step is the isolation of cells, e.g., lymphocytes, splenocytes, or B cells, from the immunized non-human mammal and the subsequent fusion of those splenocytes, or B cells, or lymphocytes, with an immortalized cell in order to form an antibody-producing hybridoma. Accordingly, the term "preparing antibodies from an immunized animal," as used herein, includes obtaining B-cells/splenocytes/lymphocytes from an immunized animal and using those cells to produce a hybridoma that expresses antibodies, as well as obtaining antibodies directly from the serum of an immunized animal. The isolation of splenocytes, e.g., from a non-human mammal is well-known in the art and, e.g., involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the antibody-producing cells are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas can be grown on a feeder layer of macrophages. The macrophages are preferably from littermates of the non-human mammal used to isolate splenocytes and are typically primed with incomplete Freund's adjuvant or the like several days before plating the hybridomas. Fusion methods are described, e.g., in (Goding, "Monoclonal Antibodies: Principles and Practice," pp. 59-103 (Academic Press, 1986)), the disclosure of which is herein incorporated by reference.

The cells are allowed to grow in the selection media for sufficient time for colony formation and antibody production. This is usually between 7 and 14 days. The hybridoma colonies are then assayed for the production of antibodies that specifically recognize the desired substrate, e.g. an NK cell receptor such as KIR2DS2. The assay is typically a colorimetric ELISA-type assay, although any assay may be employed that can be adapted to the wells that the hybridomas are grown in. Other assays include immunoprecipitation and radioimmunoassay. The wells positive for the desired antibody production are examined to determine if one or more distinct colonies are present. If more than one colony is present, the cells may be re-cloned and grown to ensure that only a single cell has given rise to the colony producing the desired antibody. Positive wells with a single apparent colony are typically recloned and re-assayed to ensure that only one monoclonal antibody is being detected and produced.

Hybridomas that are confirmed to be producing a monoclonal antibody of this invention are then grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

In preferred embodiments, the DNA encoding an antibody that binds a determinant present on an NK cell receptor is isolated from the hybridoma, placed in an appropriate expression vector for transfection into an appropriate host. The host is then used for the recombinant production of the antibody, variants thereof, active fragments thereof, or humanized or chimeric antibodies comprising the antigen recognition portion of the antibody. Preferably, the DNA used in this embodiment encodes an antibody that recognizes a determinant present on one or more human NK receptors, particularly NK receptors that are predominantly displayed in LGL cells from a significant fraction of patients with NK-LDGL.

DNA encoding the monoclonal antibodies of the invention can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding the antibody is well known in the art (see, for example, Skerra et al. (1993) Curr. Op. Immunol. 5:256; and Pluckthun (1992) Immunol. Revs. 130:151. Antibodies may also be produced by selection of combinatorial libraries of immunoglobulins, as disclosed for instance in Ward et al. (1989) Nature 341:544.

In a specific embodiment, the antibody binds essentially the same epitope or determinant as one of the monoclonal antibodies EB6b, GL183, FES172, Z27, Q66, XA185, Z270 (CNCM Ref. 3549), Z199 (Beckman Coulter, AZ20 (CNCM Ref. 1-2576), Bab281, KL247 or product ref. 195314 (R&D Systems, Minneapolis) or F278 (see, e.g., Zambello et al. (2003) Blood 102:1797) or one of the monoclonal antibodies 1D11, BAT221, ECM217, and ON72 (see, e.g. Groh et al. (2003) PNAS 100:9452-57; André et al. (2004) Eur. J. Immunol. 34:1-11, the entire disclosure of the foregoing three references incorporated by reference). The term "binds to substantially the same epitope or determinant as" the monoclonal antibody x means that an antibody "can compete" with x, where x is EB6b, etc. The identification of one or more antibodies that bind(s) to substantially the same epitope as the monoclonal antibody in question can be readily determined using any one of variety of immunological screening assays in which antibody competition can be assessed. Such assays are routine in the art (see, e.g., U.S. Pat. No. 5,660,827, which is herein incorporated by reference). It will be understood that actually determining the epitope to which the antibody binds is not in any way required to identify an antibody that binds to the same or substantially the same epitope as the monoclonal antibody in question.

For example, where the test antibodies to be examined are obtained from different source animals, or are even of a different Ig isotype, a simple competition assay may be employed in which the control (e.g. GL183) and test antibodies are admixed (or pre-adsorbed) and applied to a sample containing the epitope-containing protein, e.g. KIR2DS2 in the case of GL183. Protocols based upon ELISAs, radioimmunoassays, Western blotting and the use of BIACORE (as described, e.g., in the examples section) are suitable for use in such simple competition studies and are well known in the art.

In certain embodiments, one would pre-mix the control antibodies (e.g. GL183) with varying amounts of the test antibodies (e.g., 1:10 or 1:100) for a period of time prior to applying to the antigen (e.g. KIR2DS2 epitope) containing sample. In other embodiments, the control and varying amounts of test antibodies can simply be admixed during exposure to the antigen sample. As long as one can distinguish bound from free antibodies (e.g., by using separation or washing techniques to eliminate unbound antibodies) and the control antibody from the test antibodies (e.g., by using species- or isotype-specific secondary antibodies or by specifically labeling the control antibody with a detectable label) one will be able to determine if the test antibodies reduce the binding of the control antibody to the antigen, indicating that the test antibody recognizes substantially the same epitope as the control. The binding of the (labeled) control antibodies in the absence of a completely irrelevant antibody would be the control high value. The control low value would be obtained by incubating the labeled control antibodies (e.g. GL183) with unlabeled antibodies of exactly the same type (e.g. GL183), where competition would occur and reduce binding of the labeled antibodies. In a test assay, a significant reduction in labeled antibody reactivity in the presence of a test antibody is indicative of a test antibody that recognizes the same epitope, i.e., one that "cross-reacts" with the labeled control antibody. Any test antibody that reduces the binding of the labeled control to each the antigen by at least 50% or more preferably 70%, at any ratio of control:test antibody between about 1:10 and about 1:100 is considered to be an antibody that binds to substantially the same epitope or determinant as the control. Preferably, such test antibody will reduce the binding of the control to the antigen by at least 90%.

In one embodiment, competition can be assessed by a flow cytometry test. Cells bearing a given activating receptor are incubated first with a control antibody that is known to specifically bind to the receptor (e.g., NK cells expressing KIR2DL2, and the GL183 antibody), and then with the test antibody that has been labeled with, e.g., a fluorochrome or biotin. The test antibody is said to compete with the control if the binding obtained with preincubation with saturating amounts of control antibody is 80%, preferably, 50, 40 or less of the binding (mean of fluorescence) obtained by the antibody without preincubation with the control. Alternatively, a test antibody is said to compete with the control if the binding obtained with a labeled control (by a fluorochrome or biotin) on cells preincubated with saturating amount of antibody to test is 80%, preferably 50%, 40%, or less of the binding obtained without preincubation with the antibody.

In one preferred example, a simple competition assay may be employed in which a test antibody is pre-adsorbed and applied at saturating concentration to a surface onto which is immobilized the substrate for the antibody binding, e.g. the KIR2DS2 protein, or epitope-containing portion thereof, which is known to be bound by GL183. The surface is preferably a BIACORE chip. The control antibody (e.g. GL183) is then brought into contact with the surface at a substrate-saturating concentration and the substrate surface binding of the control antibody is measured. This binding of the control antibody is compared with the binding of the control antibody to the substrate-containing surface in the absence of test antibody. In a test assay, a significant reduction in binding of the substrate-containing surface by the control antibody in the presence of a test antibody is indicative of a test antibody that recognizes the same epitope, i.e., one that "cross-reacts" with the control antibody. Any test antibody that reduces the binding of the control antibody to the antigen-containing substrate by at least 30% or more preferably 40% is considered to be an antibody that binds to substantially the same epitope or determinant as the control antibody. Preferably, such test antibody will reduce the binding of the control antibody to the substrate by at least 50%. It will be appreciated that the order of control and test antibodies can be reversed, that is the control antibody is first bound to the surface and the test antibody is brought into contact with the surface thereafter.

Preferably, the antibody having higher affinity for the substrate antigens is bound to the substrate-containing surface first since it will be expected that the decrease in binding seen for the second antibody (assuming the antibodies are cross-reacting) will be of greater magnitude. Further examples of such assays are provided in the Examples and in Saunal et al. (1995) J. Immunol. Meth 183: 33-41, the disclosure of which is incorporated herein by reference.

In one embodiment, antibodies capable of interacting with multiple receptors on the NK cell surface, e.g. any combination of two or more NK cell receptors such as KIR receptors (KIR2DL1, KIR2DS1, KIR2DL2, KIR2DL3, KIR2DS2, KIR2DS4, KIR3DL1, KIR3DS1, or KIR3DL2, or any combination involving one or more of these receptors) or NKG2 receptors (NKG2A, NKG2C, NKG2D, NKG2E, NKG2F, or any combination involving one or more of these receptors) and any additional NK cell receptor or receptors, may be obtained, particularly if it is ensured that the antibodies do not show excessive cross-reactivity with other, unrelated proteins. Preferably, monoclonal antibodies that recognize an epitope from an NK cell receptor, e.g. a KIR2DL2 epitope, will react with an epitope that is present on a substantial percentage NK cells, especially from patients, but will not significantly react with $CD3^+$ T cells, with $CD20^+$ B cells, or with other immune or non-immune cells. In preferred embodiments, the antibody will also be nonreactive with monocytes, granulocytes, platelets, and red blood cells. In preferred embodiments, the antibodies will only recognize a single NK cell receptor, thereby restricting as much as possible the effects of the therapeutic (e.g., cytotoxic) antibodies to the overproliferating cells underlying the disorder.

Once an antibody that specifically recognizes one, or possibly a small number of, receptors on NK cells, preferably human NK cells, is identified, it can be tested for its ability to bind to immune cells (preferably NK) cells taken from patients with the immunoproliferative disorder.

Typically, the antibodies are validated in an immunoassay to test its ability to bind to NK cells taken from patients with the immunoproliferative disorder. For example, peripheral blood lymphocytes (PBLs) are taken from a plurality of patients, and NK cells are enriched from the PBLs using antibodies to receptors present on NK cells, such as CD56 (see, e.g., Zambello et al. (2003) Blood 102:1797). The ability of a given antibody to bind to the NK cells is then assessed using standard methods well known to those in the art. In one embodiment, each sample of cells is incubated individually with various antibodies that are each specific to a particular NK cell receptor. Antibodies that are found to bind to a substantial proportion of NK cells (e.g., 20%, 30%, 40%, 50%, 60%, 70%, 80% or more) from a significant percentage of patients (e.g., 5%, 10%, 20%, 30%, 40%, 50% or more) are suitable for use in the present invention, both for diagnostic purposes during the NK receptor status typing step described herein, or for use in the herein-described therapeutic methods, e.g., for derivitization to form human-suitable, cytotoxic antibodies. To assess the binding of the antibodies to the cells, the antibodies can either be directly or indirectly labeled. When indirectly labeled, a secondary, labeled antibody is typically added. The binding of the antibodies to the cells can then be detected using, e.g., cytofluorometric analysis (e.g. FACScan). See, e.g., Zambello et al. (2003) Blood 102:1797 or any other standard method. It will be appreciated that the procedure can also be carried out analogously with T cells and T cell receptor; this can be carried out using T cells from patients with an immunoproliferative disorder (e.g. T cell LDGL, rheumatoid arthritis, etc.) and the T cells may be $CD3^+$ and optionally $CD4^+CD28^-$ or $CD8^+$.

It is expected that a small number (e.g., 1, 2, 3, 4, 5, 6, 7, 8, 9, 10, 11, 12, 13, 14, 15, 16, 17, 18, 19, or 20) of antibodies will be sufficient to detect and target most of the overproliferating (e.g. NK) cells in most patients with disorders such as NK-LDGL, autoimmune or inflammatory disorders. Accordingly, it will be possible to assemble small panels of diagnostic (directly or indirectly labeled) and therapeutic (human-suitable, optionally toxic) antibodies that would generally be sufficient to type and treat virtually all patients (using either a single or small combination of antibodies) using the present methods. Such panels may ultimately be made available as a kit, preferably complete with instructions for using the antibodies.

The panels of antibodies produced according to the present invention, therefore, will include those that are specific for one or a small number of NK receptor types. In addition, in some embodiments, multiple antibodies will be prepared against a given receptor, to ensure maximum targeting of the receptor-expressing cells in vivo in all patients and also to ensure that polymorphic receptors are effectively targeted in a maximum number of patients.

In other embodiments, it will be appreciated that an antibody for use in the diagnostic (directly or indirectly labeled) and therapeutic (human-suitable, optionally toxic) embodiments of the present invention may recognize multiple NK receptors (e.g. 2, 3, 4 or more NK receptors. For example the antibody can recognize a plurality of NCRs, or KIR (e.g. KIR2DL1, KIR2DL2/3, etc.), or a plurality or KIR activatory receptors or KIR inhibitory receptors. Furthermore, it will be possible to use multiple antibodies (e.g. at least 2, 3, 4 etc.), at least one recognizing multiple NK receptors. Examples of antibodies that recognize multiple NK receptors are provided in PCT Publication No. WO 2005/0031172 (Innate Pharma), the disclosure of which is incorporated herein by reference in its entirety.

Producing Antibodies Suitable for Use in Humans

Once monoclonal antibodies are produced, generally in non-human animals, that can specifically bind to one or more NK receptors commonly present on LGL (e.g. NK) cells of NK-LDGL patients, the antibodies will generally be modified so as to make them suitable for therapeutic use in humans. For example, they may be humanized, chimerized, or selected from a library of human antibodies using methods well known in the art. Such human-suitable antibodies can be used directly in the present therapeutic methods, or can be further derivatized into cytotoxic antibodies, as described infra, for use in the methods.

In one, preferred, embodiment, the DNA of a hybridoma producing an antibody of this invention, e.g. a GL183-like antibody, can be modified prior to insertion into an expression vector, for example, by substituting the coding sequence for human heavy- and light-chain constant domains in place of the homologous non-human sequences (e.g., Morrison et al. (1984) PNAS 81:6851), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

In one particularly preferred embodiment, the antibody of this invention is humanized. "Humanized" forms of antibodies according to this invention are specific chimeric immunoglobulins, immunoglobulin chains or fragments thereof (such as Fv, Fab, Fab', F(ab')$_2$, or other antigen-binding subsequences of antibodies) which contain minimal sequence derived from the murine or other non-human immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. For further details see Jones et al. (1986) Nature 321: 522; Reichmann et al. (1988) Nature 332: 323; Verhoeyen et al. (1988) Science 239:1534 (1988); Presta (1992) Curr. Op. Struct. Biol. 2:593; each of which is herein incorporated by reference in its entirety.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al. (1993) J. Immun., 151:2296; Chothia and Lesk (1987) J. Mol. Biol. 196:901). Another method uses a particular framework from the consensus sequence of all human antibodies of a particular subgroup of light or heavy chains. The same framework can be used for several different humanized antibodies (Carter et al. (1992) PNAS 89:4285; Presta et al. (1993) J. Immunol. 51:1993)).

It is further important that antibodies be humanized while retaining their high affinity for one or more NK cell receptors, preferably human receptors, and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Human antibodies may also be produced according to various other techniques, such as by using, for immunization, other transgenic animals that have been engineered to express a human antibody repertoire. In this technique, elements of the human heavy and light chain loci are introduced into mice or other animals with targeted disruptions of the endogenous heavy chain and light chain loci (see, e.g., Jakobovitz et al. (1993) Nature 362:255; Green et al. (1994) Nature Genet. 7:13; Lonberg et al. (1994) Nature 368:856; Taylor et al. (1994) Int. Immun. 6:579, the entire disclosures of which are herein incorporated by reference). Alternatively, human antibodies can be constructed by genetic or chromosomal transfection methods, or through the selection of antibody repertoires using phage display methods. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell (see, e.g., Johnson et al. (1993) Curr Op Struct Biol 3:5564-571; McCafferty et al. (1990) Nature 348:552-553, the entire disclosures of which are herein incorporated by reference). Human antibodies may also be generated by in vitro activated B cells (see, e.g., U.S. Pat. Nos. 5,567,610 and 5,229,275, the disclosures of which are incorporated in their entirety by reference).

In one embodiment, "humanized" monoclonal antibodies are made using an animal such as a XenoMouse® (Abgenix, Fremont, Calif.) for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. An analogous method can be achieved using a HuMAb-Mouse™ (Medarex).

The antibodies of the present invention may also be derivatized to "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (see, e.g., Morrison et al. (1984) PNAS 81:6851; U.S. Pat. No. 4,816,567).

While antibodies in underivatized (e.g. "naked" antibodies) or unmodified form, particularly of the IgG1 or IgG3 type are expected to inhibit the proliferation of the overproliferating NK cells or be cytotoxic towards overproliferating or NK unwanted NK cells such as in those from a NK-LDGL or rheumatoid arthritis patient, it is also possible to prepare derivatized antibodies to make them cytotoxic. In one embodiment, once the NK cell receptor specific antibodies are isolated and rendered suitable for use in humans, they will be derivatized to make them toxic to cells. In this way, administration of the antibody to patients will lead to the relatively specific binding of the antibody to overproliferating NK cells, thereby directly killing or inhibiting the cells underlying the disorder. Because of the specificity of the treatment, other, non-overproliferating cells of the body, including most other NK cells as well as other cells of the immune system, will be minimally affected by the treatment.

Any of a large number of toxic moieties or strategies can be used to produce such antibodies. In certain, preferred embodiments, the antibodies will be directly derivatized with radioisotopes or other toxic compounds. In such cases, the labeled monospecific antibody can be injected into the patient, where it can then bind to and kill cells expressing the target antigen, with unbound antibody simply clearing the body. Indirect strategies can also be used, such as the "Affinity Enhancement System" (AES) (see, e.g., U.S. Pat. No. 5,256,395; Barbet et al. (1999) Cancer Biother Radiopharm 14:153-166; the entire disclosures of which are herein incorporated by reference). This particular approach involves the use of a radiolabeled hapten and an antibody that recognizes both the NK cell receptor and the radioactive hapten. In this case, the antibody is first injected into the patient and allowed to bind to target cells, and then, once unbound antibody is allowed to clear from the blood stream, the radiolabeled hapten is administered. The hapten binds to the antibody-antigen complex on the overproliferating or unwanted cells (e.g. NK or T) cells, thereby killing them, with the unbound hapten clearing the body. Any type of moiety with a cytotoxic or cytoinhibitory effect can be used in conjunction with the present antibodies to inhibit or kill specific NK receptor expressing cells, including radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, camptothecans, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, abrin, 5-fluorouridine, ribonuclease (RNase), DNase I, Staphylococcal enterotoxin-A, pokeweed antiviral protein, gelonin, diphtherin toxin, *Pseudomonas* exotoxin, and *Pseudomonas* endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

The toxins or other compounds can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56: 244; Wong, Chemistry of Protein Conjugation and Cross-linking (CRC Press 1991); Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chemistry 8:3; Reisfeld et al. (1989) Antibody, Immunicon. Radiopharm. 2:217; the entire disclosures of each of which are herein incorporated by reference).

In one, preferred, embodiment, the antibody will be derivatized with a radioactive isotope, such as I-131. Any of a number of suitable radioactive isotopes can be used, including, but not limited to, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

In selecting a cytotoxic moiety for inclusion in the present methods, it is desirable to ensure that the moiety will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "significant side effects", as used herein, refers to an antibody, ligand or antibody conjugate, that, when administered in vivo, will produce only negligible or clinically manageable side effects, such as those normally encountered during chemotherapy.

Testing the Cytotoxic Antibodies for Binding and Cytotoxic Activity

Once antibodies are obtained that are known to specifically bind to NK cell receptors on cells from patients with immunoproliferative disorders, and which have been rendered suitable for use in humans, and optionally derivatized to include a toxic moiety, they will generally be assessed for their ability to interact with, affect the activity of, and/or kill target cells. In general, the assays described above for detecting antibody binding to NK cells or NK cell receptors, including competition-based assays, ELISAs, radioimmunoassays, Western blotting, BIACORE-based assays, and flow cytometry assays, can be equally applied to detect the interaction of humanized, chimeric, or other human-suitable, NK cell antibodies, such as cytotoxic antibodies, with their target cells. Typically, target cells will be NK cells taken from patients with an immunoproliferative disorder.

In the present assays, the ability of the humanized or human-suitable, therapeutic (e.g. cytotoxic) antibody to bind to the target cell or human NK cell receptor will be compared with the ability of a control protein, e.g. an antibody raised against a structurally unrelated antigen, or a non-Ig peptide or protein, to bind to the same target. Antibodies or fragments that bind to the target cells or NK cell receptor using any suitable assay with 25%, 50%, 100%, 200%, 1000%, or higher increased affinity relative to the control protein, are said to "specifically bind to" or "specifically interact with" the target, and are preferred for use in the therapeutic methods described below.

In addition to binding, the ability of the antibodies to inhibit the proliferation of, or, preferably, kill, target cells can be assessed. In one embodiment, human NK cells expressing one or more relevant receptors, e.g. LGL or NK cells taken from NK-LDGL patients, are introduced into plates, e.g., 96-well plates, and exposed to various amounts of the relevant antibodies. By adding a vital dye, i.e. one taken up by intact cells, such as AlamarBlue (BioSource International, Camarillo, Calif.), and washing to remove excess dye, the number of viable cells can be measured by virtue of the optical density (the more cells killed by the antibody, the lower the optical density). (See, e.g., Connolly et al. (2001) J Pharm Exp Ther 298:25-33, the disclosure of which is herein incorporated by reference in its entirety). Any other suitable in vitro cytotoxicity assay, assay to measure cell proliferation or survival, or assay to detect NK cell activity can equally be used, as can in vivo assays, e.g. administering the antibodies to animal models, e.g., mice, containing human NK cells expressing the relevant receptor, and detecting the effect of the antibody administration on the survival or activity of the human NK cells over time. Also, where the antibody cross-reacts with a non-human receptor, e.g., a primate NK cell receptor, the therapeutic antibodies can be used in vitro or in vivo to assess the ability of the antibody to bind to and/or kill NK cells from the animal that express the relevant receptor.

Any antibody, preferably a human-suitable antibody, e.g. a cytotoxic antibody, that can detectably slow, stop, or reverse the proliferation of the overproliferating NK cells, in vitro or in vivo, can be used in the present methods. Preferably, the antibody is capable of stopping the proliferation (e.g., preventing an increase in the number of NK cells in vitro or in vivo expressing the targeted NK cell receptor), and most preferably the antibody can reverse the proliferation, leading to a decrease in the total number of such cells. In certain embodiments, the antibody is capable of producing a 10%, 20%, 30%, 40%, 50%, 60%, 70%, 80%, 90%, 95%, 96%, 97%, 98%, 99%, or 100% decrease in the number of NK cells expressing the targeted receptor.

In one preferred embodiment, therefore, the present invention provides a method for producing an antibody suitable for use in the treatment of an immunoproliferative disorder, the method comprising the following steps: a) providing a plurality of antibodies that specifically bind to receptors present on the surface of NK cells; b) testing the ability of the antibodies to bind to NK cells taken from one or more patients with the immunoproliferative disorder; c) selecting an antibody from said plurality that binds to a substantial number of NK cells taken from one or more of said patients; and d) making said antibody suitable for human administration. In one embodiment, the method further comprises a step in which a cytotoxic agent is linked to said antibody. In such methods, "substantial number" can mean e.g., 30%, 40%, 50%, preferably 60%, 70%, 80%, 90% or a higher percentage of the cells.

The present invention also provides a related method, comprising the following steps: a) providing an antibody that specifically binds to NK cells taken from one or more patients with NK-LDGL; b) testing the ability of the antibody to bind to NK cells taken from one or more patients with NK-LDGL; and c) if the antibody binds to a substantial number of NK cells taken from one or more of the patients, making the antibody suitable for human administration. In one embodiment, the method further comprises a step in which a cytotoxic agent is linked to the antibody. It will be appreciated that such methods, as well as the methods described elsewhere in the present specification, including in the preceding paragraph, can be equally performed using cells other than NK cells, e.g., T cells, LGL cells, and for the treatment of disorders other than NK-LDGL, e.g. T cell LDGL or other immunoproliferative disorders.

It will be appreciated that equivalent methods can be used to produce antibodies suitable for treating animals, or for testing in an animal model. In that case, the antibodies will be ensured to be capable of specifically recognizing NK cell receptors from the relevant animal, and prevalent in an animal disease involving clonal expansion of NK or other cells. Similarly, the antibody will be modified to be suitable for administration into the particular animal.

Model to Test Inflammation In Vivo

The anti-inflammatory effects of depleting CD94/NKG2A and/or C expressing cells on inflammation in vivo can be assessed in mouse models. A depleting antibody against CD94/NKG2A and/or -C, such as the mouse CD94/NKG2A, -C and -E targeting rat mAb 20D5, is be used to deplete specific lymphocyte populations in mice, e.g in murine models for chronic inflammation. Examples of such models include the collagen-induced arthritis (CIA) model, which is an in vivo model to study Rheumatoid Arthritis, or experimental autoimmune encephalomyelitis (EAE), which is a mouse model for human multiple sclerosis. In such models, mAb's that deplete CD94/NKG2A and -C cells could be injected either before, during or after onset of inflammation, and the reduction of inflammation could be assessed with techniques known in the art to measure the intensity of inflammation in these models (e.g. physiologically or by immuno-histochemistry).

Administration of Antibodies for Treatment Methods

The antibodies produced using the present methods are particularly effective at treating proliferative disorders, especially immunoproliferative disorders. In general, the present methods can be used to treat any disorder caused by the presence or excess of any cells expressing one or a small number of NK cell receptors, and which can therefore be effectively treated by selectively killing or inhibiting cells expressing particular NK cell receptors. Other suitable diseases include T-cell type LDGL, autoimmune disorders, and any other immunoproliferative or malignant disorders involving NK or related cells, including T cells which are $CD3^+$ and optionally $CD4^+$ $CD28^-$ or $CD8^+$. "Immunoproliferative diseases" refer to any disorder, condition, or disease characterized or caused by excessive or uncontrolled inflammation, or any aspect of inflammation such as redness, swelling, heat, pain, etc., and specifically including inflammatory disease and autoimmune disorder. Inflammatory diseases include allergies, including allergic rhinitis/sinusitis, skin allergies such as urticaria/hives, angioedema, atopic dermatitis, food allergies, drug allergies, insect allergies, and allergic disorders such as mastocytosisasthma, asthma, arthritis, including osteoarthritis, rheumatoid arthritis, and spondyloarthropathies, gastrointestinal inflammation, Crohn's disease and ulcerative colitis, neuroinflammatory disorders, and autoimmune disorders.

"Autoimmune" disorders include any disorder, condition, or disease in which the immune system mounts a reaction against self cells or tissues, due to a breakdown in the ability to distinguish self from non-self or otherwise. Examples of autoimmune disorders include Hashimoto's thyroiditis, pernicious anemia, Addison's disease, type I diabetes, rheumatoid arthritis, systemic lupus erythematosus, dermatomyositis, psoriasis, Sjogren's syndrome, lupus erythematosus, demyelinating conditions, multiple sclerosis, myasthenia gravis, Reiter's syndrome, Grave's disease, polymyositis, Guillain Barré, Wegener's granulomatosus, celiac disease, polyarteritis nodosa, polymyalgia rheumatica, temporal arteritis, Bechet's disease, Churg-Strauss syndrome, Takayasu's arteritis, and others. Autoimmune disorders can involve any component of the immune system, and can target any cell or tissue type in the body.

As used herein, the term rheumatoid arthritis refers to any disorder involving inflammation of the joints, and including features such as joint erosion, lymphocyte infiltration, synovial hyperplasia, aggressive proliferation of fibroblast-like synoviocytes and macrophages, and/or the presence of T or NK cells (e.g. NK cells which $CD56^+$; T cells which are $CD3^+$ and optionally $CD4^+$ $CD28^-$ or $CD8^+$), and are also any one or more of $KIR2DL1^+$, $KIR2DL2^+$, $KIR2DL3^+$, $KIR2DL5A^+$, $KIR2DL5B^+$, $KIR3DL1^+$, $KIR3DL2^+$, $KIR3DL3^+$, $KIR2DS1^+$, $KIR2DS2^+$, $KIR2DS3^+$, $KIR2DS4^+$, $KIR2DS5^+$, $KIR3DS1^+$, $CD94^+$, $NKG2A^+$, $NKG2C^+$, $NKG2D^+$, $NKG2E^+$, $NKG2F^+$, $NKG2G^+$, $NKp30^+$, $NKp44^+$, $NKp46^+$. Particularly when the cell type present is a T cell, the T or NK cell receptor targeted by the antibody of the invention is an NKG2 protein, preferably NKG2D. Generally, in established rheumatoid arthritis, the synovium thickens, the cartilage and the underlying bone begins to disintegrate and evidence of joint destruction accrues.

In one embodiment, the disease treated in accordance with the invention is an established immunoproliferative disorder, generally a characterized by tissue injury or damage and/or persisting disease (e.g. inflammation, symptoms or tissue injury) for at least 3, 6, 9, 12, 24 or 36 months.

In one embodiment, a component of the present therapeutic methods is a typing step in which the predominant receptor or receptors on the expanded NK or other cells in patients is identified. Generally, in this step, a sample of NK cells or other (e.g. T cells, LGL cells) is taken from a patient, and tested, e.g., using immunoassays, to determine the relative prominence of various NK cell receptors on the cells. While NK cells are preferred for this method, it will be appreciated that any cell type that expresses NK cell receptors can be used (e.g. T cells which are $CD3^+$ and optionally $CD4^+$ $CD28^-$ or $CD8^+$). Ideally, this step is performed using a kit containing a panel of antibodies, either directly or indirectly labeled, that together recognize the various NK cell receptors that are most commonly found in proliferating NK cells in the immunoproliferative disorders. Often, one or a small number of receptors will be found to be present on a substantial number, e.g., 30%, 40%, 50% of the cells, preferably 60%, 70%, 80%, 90% or higher. In that case, then a single or small number of therapeutic (e.g. cytotoxic) antibody or antibodies, i.e. those specifically directed against the detected receptor or receptors, can be administered. In that way, the overproliferating or unwanted cells will be specifically targeted.

In addition to the immunological assays described above, other methods can also be used to determine the identity of and relative expression level of the various NK cell receptors or NK cells taken from patients. For example, RNA-based methods, e.g., RT-PCR or Northern blotting, can be used to examine the relative transcription level of various NK cell receptors in cells taken from a patient. In many cases, a single or small number of receptor-specific transcripts will predominate, allowing treatment of the patient using cytotoxic antibodies specific to the particular receptor(s) encoded by the transcript(s).

In another embodiment, insight into the identity of NK cell receptors expressed on proliferating immune cells (e.g. NK) cells in patients can be gained by genotyping. For example, 20 or more different KIR haplotypes have been identified, and at least 40 distinct genotypes (see, e.g., Hsu et al. (2002) Immunol Rev. 190:40-52, which is herein incorporated by reference in its entirety). Some of these haplotypes and genotypes are associated with activating or inhibitory KIR receptor expression. Accordingly, a determination that a patient possesses a particular haplotype or a particular genotype can often indicate which receptors are most likely to be expressed in the patient's NK cells. In some cases, certain haplotypes or genotypes in patients may be reliably associated with a particular expression pattern or NK receptor status, thereby allowing the selection of particular therapeutic (e.g. cytotoxic) antibodies for use in the present therapeutic methods.

In another embodiment, functional assays to assess the activity of the immunoproliferative (preferably NK) cells in patients will be used, alone or in conjunction with other methods, e.g., immunological, RNA-based, or genotyping methods. As one or more activating-NK cell receptors may predominate in many patients, a finding that cells taken from a particular patient are particularly active (as determined using any standard assay, e.g. cytolytic assays, cytokine production, intracellular free calcium, etc.) will provide important information about which receptors may be expressed in the proliferating cells. Such information, particularly when combined with other results, can be used to decide which cytotoxic antibody or antibodies are be used to achieve the most specific therapeutic strategy. For example, a finding that a majority of the NK cells from a particular NK-LDGL patient are specifically recognized by the GL183 antibody (which recognizes both the inhibitory KIR2DL2 and KIR2DL3 receptors and the activating KIR2DS2 receptor), combined with a finding that most of the NK cells are also active, could be used to conclude that the ideal treatment would involve a single cytotoxic antibody specific to NKR2DS2, but not to KIR2DL2 or KIR2DL3. Ideally, the present treatment methods target the maximum proportion of overproliferating NK- or NK-like cells using the minimum number of therapeutic antibodies.

Ideally, in developing the present antibodies, methods for using them, and kits, a number of patients will be screened with a number of different antibodies directed against different NK cell receptors. In that way, a panel of diagnostic and therapeutic (e.g. cytotoxic) antibodies can be assembled that will cover the majority of expanded NK cells in most patients. For example, if it is determined that one of the KIR receptors (e.g., KIR2DS2) is expressed in at least 50% of the expanded cells in a substantial percentage (e.g. 25%, 50%, or higher) of patients with NK-LDGL, then a kit produced according to the present invention will generally include at least one diagnostic antibody against that receptor, as well as one or more therapeutic antibodies against the receptor. This is particularly true if the receptor is specific to NK cells, i.e., is not expressed on any other cell type, although receptors that are also expressed on other cell types can also be included. In particular, a therapeutic antibody that specifically binds a receptor that is non-NK cell specific may be used if it is the only way to target a substantial fraction of NK cells in the patient. Depending on the type of non-NK cell type involved, the form or timing of administration of the therapeutic antibody may be specifically tailored to maximize its interaction with NK cells and minimize its interaction with the non-NK cell type (e.g., if the receptor is also expressed in immature B or T cells, administering the antibody in a way that minimizes its contact with the bone marrow or thymus).

The kits of the present invention may contain any number of diagnostic and/or therapeutic antibodies, e.g., 1, 2, 3, 4, 5, 6, 7, 8, 9, 10, 11, 12, 13, 14, 15, 16, 17, 18, 19, 20, 25, 30, or any other number of diagnostic and/or therapeutic antibodies. In such kits, the diagnostic antibodies will often be labeled, either directly or indirectly (e.g., using secondary antibodies). Therapeutic antibodies can be unmodified, i.e. without any linked cytotoxic or other moieties, working by, for example, simply binding to target cells and thereby inactivating them, triggering cell death, or marking them for destruction by the immune system. In other embodiments, the therapeutic antibodies will be linked to one or more cytotoxic moieties. It will be appreciated that this description of the contents of the kits is not limiting in any way. For example, for the therapeutic antibodies, the kit may contain any combination of unmodified or cytotoxic antibodies. In addition, the kit may contain other types of therapeutic compounds as well, such as chemotherapeutic or anti-proliferative agents. Preferably, the kits also include instructions for using the antibodies, e.g., detailing the herein-described methods for typing NK receptor status in patients and administering therapeutic antibodies accordingly.

It will also be appreciated that the administration of therapeutic antibodies can involve the administration of 1, 2, 3, 4, 5, 6, 7, 8, 9, 10, or any number of different antibodies, directed against a single or multiple NK cell receptors as appropriate, in particular in view of the NK receptor status as determined in the typing step described supra. Such combinations of antibodies can be administered together, or separately, depending, e.g., on the relative toxicity of each of the antibodies, the NK receptor status of the patient, or other factors.

In addition, the treatment may involve multiple rounds of therapeutic (e.g. cytotoxic) antibody administration. For example, following an initial round of antibody administration, the overall number of NK or LGL cells in the patient will generally be re-measured, and, if still elevated, an additional round of NK receptor status typing can be performed, followed by an additional round of therapeutic antibody administration. It will be appreciated that the cytotoxic antibodies administered in this additional round of administration will not necessarily be identical to those used in the initial round, but will depend primarily on the results of the additional typing step. In this way, multiple rounds of NK receptor status typing and therapeutic antibody administration can be performed, e.g., until the LGL or NK cell proliferation is brought under control.

The invention also provides compositions, e.g., pharmaceutical compositions, that comprise any of the present antibodies, including fragments and derivatives thereof, in any suitable vehicle in an amount effective to inhibit the proliferation or activity of, or to kill, cells expressing the targeted NK cell receptor in patients. The composition generally further comprises a pharmaceutically acceptable carrier. It will be appreciated that the present methods of administering antibodies and compositions to patients can also be used to treat animals, or to test the efficacy of any of the herein-described methods or compositions in animal models for human diseases.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added.

For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, ophthalmically, by nasal aerosol or inhalation.

Such compositions are prepared according to techniques well-known in the art of pharmaceutical formulation.

In one embodiment, the antibodies of this invention may be incorporated into liposomes ("immunoliposomes"), alone or together with another substance for targeted delivery to a patient or an animal. Such other substances can include nucleic acids for the delivery of genes for gene therapy or for the delivery of antisense RNA, RNAi or siRNA for suppressing a gene in an NK cell, or toxins or drugs for the activation of NK cells through other means, or any other agent described herein that may be useful for activation of NK cells or targeting of tumor or infected cells.

In another embodiment, the antibodies of the invention can be modified to improve its bioavailability, half life in vivo, etc. For example, the antibodies can be pegylated, using any of the number of forms of polyethylene glycol and methods of attachment known in the art (see, e.g., Lee et al. (2003) Bioconjug Chem. 14(3):546-53; Harris et al. (2003) Nat Rev Drug Discov. 2(3):214-21; Deckert et al. (2000) Int J Cancer. 87(3):382-90).

Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar administration regimens (i.e., formulations and/or doses and/or administration protocols) may be used with the antibodies of this invention. Schedules and dosages for administration can be determined in accordance with known methods for these products, for example using the manufacturers' instructions. For example, a monoclonal antibody can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody of the invention may between about 10 mg/m2 and 500 mg/m2. However, it will be appreciated that these schedules are exemplary and that optimal schedule and regimen can be adapted taking into account the affinity of the antibody and the tolerability of the antibodies that must be determined in clinical trials. Quantities and schedule of injection of antibodies to NK cell receptors that saturate NK cells for 24 hours, 48 hours 72 hours or a week or a month will be determined considering the affinity of the antibody and the its pharmacokinetic parameters.

According to another embodiment, the antibody compositions of this invention may further comprise one or more additional therapeutic agents, including agents normally utilized for the particular therapeutic purpose for which the antibody is being administered. The additional therapeutic agent will normally be present in the composition in amounts typically used for that agent in a monotherapy for the particular disease or condition being treated. Such therapeutic agents include, but are not limited to, therapeutic agents used in the treatment of cancers, therapeutic agents used to treat inflammatory or autoimmune disorders, infectious disease, therapeutic agents used in other immunotherapies, cytokines (such as IL-2 or IL-15), other antibodies and fragments of other antibodies. So long as a particular therapeutic approach is not known to be detrimental to the patient's condition in itself, and does not significantly counteract the NK cell receptor antibody-based treatment, its combination with the present invention is contemplated.

As chemotherapy is often used to treat proliferative disorders such as NK-LDGL, in particular NK-LDGL leukemia, the NK cell receptor antibody therapeutic compositions of the present invention may be administered in combination with other chemotherapeutic or hormonal therapy agents. A variety of hormonal therapy and chemotherapeutic agents may be used in the combined treatment methods disclosed herein. Chemotherapeutic agents contemplated as exemplary include alkylating agents, antimetabolites, cytotoxic antibiotics, vinca alkaloids, for example adriamycin, dactinomycin, mitomycin, caminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s) and derivatives and prodrugs thereof. Hormonal agents include for example LHRH agonists such as leuprorelin, goserelin, triptorelin, and buserelin; anti-estrogens such as tamoxifen and toremifene; anti-androgens such as flutamide, nilutamide, cyproterone and bicalutamide; aromatase inhibitors such as anastrozole, exemestane, letrozole and fadrozole; and progestagens such as medroxy, chlormadinone and megestrol. Further useful agents include compounds that interfere with DNA replication, mitosis and chromosomal segregation, and agents that disrupt the synthesis and fidelity of polynucleotide precursors may also be used. A number of exemplary chemotherapeutic agents for combined therapy are listed in Table C of U.S. Pat. No. 6,524,583, the disclosure of which agents and indications are specifically incorporated herein by reference. Each of the agents listed are exemplary and not limiting. Another useful source is "Remington's Pharmaceutical Sciences" 15th Edition, chapter 33, in particular pages 624-652. Variation in dosage will likely occur depending on the condition being treated. The physician administering treatment will be able to determine the appropriate dose for the individual subject.

According to another important embodiment of the present invention, the NK cell receptor antibody therapeutic compositions may be administered in conjunction with one or more additional therapeutic agents normally utilized for the particular therapeutic inflammatory or autoimmune indications for which the antibody or compound is being administered, e.g. with therapeutic agents used in the treatment of rheumatoid arthritis, therapeutic agents used in the treatment of Wegener's granulomatosis, therapeutic agents used in the treatment of Sjogren's syndrome, therapeutic agents used in the treatment of insulin-dependent diabetes mellitus, cytokines such as IL-10, and compounds that counteract cytokines and other molecules that drive immune cell activation and proliferation, e.g., anti-TNF-alpha antibodies and other compounds, and anti-IL-15 antibodies and other compounds.

The present invention may be used in combination with classical approaches, such as surgery, and the like. When one or more agents or approaches are used in combination with the present therapy, there is no requirement for the combined results to be additive of the effects observed when each treatment is conducted separately. Although at least additive effects are generally desirable, any decrease in NK cell numbers, cytokine production or other beneficial effect above one of the single therapies would be of benefit. Also, there is no particular requirement for the combined treatment to exhibit synergistic effects, although this is certainly possible and advantageous. The NK cell receptor antibody therapeutic composition treatment may precede, or follow, the other treatment by, e.g., intervals ranging from minutes to weeks and months. It also is envisioned that more than one administration of either the NK cell receptor antibody therapeutic composition or the other agent will be utilized. The agents may be administered interchangeably, on alternate days or weeks; or a cycle of a NK cell receptor antibody therapeutic compositions treatment may be given, followed by a cycle of the other agent therapy. In any event, all that is required is to deliver both agents in a combined amount effective to exert a therapeutically beneficial effect, irrespective of the times for administration.

In other aspects, immunomodulatory compounds or regimens may be practiced in combination with the present invention. Preferred examples include treatment with cytokines. Various cytokines may be employed in such combined approaches. Examples of cytokines include IL-1alpha IL-1beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, IFN-gamma, or compounds (e.g. antibodies or soluble receptors that bind the cytokines) that inhibit any of these cytokines. Cytokines or their inhibitors are administered according to standard regimens, consistent with clinical indications such as the condition of the patient and the relative toxicity of the cytokine.

The present methods can also be used in combination with adjunct compounds. Adjunct compounds may include by way of example anti-emetics such as serotonin antagonists and therapies such as phenothiazines, substituted benzamides, antihistamines, butyrophenones, corticosteroids, benzodiazepines and cannabinoids; bisphosphonates such as zoledronic acid and pamidronic acid; and hematopoietic growth factors such as erythropoietin and G-CSF, for example filgrastim, lenograstim and darbepoietin.

Further aspects and advantages of this invention are disclosed in the following experimental section, which should be regarded as illustrative and not limiting the scope of this application.

Example 1

Generation of mAbs Specific to NK Cell Receptors

Novel monoclonal antibodies are generated by immunizing 5 week old Balb C mice with activated polyclonal or monoclonal NK cell lines, e.g., as described in Moretta et al. (1990) J Exp Med. 172(6):1589-98. After different cell fusions, the mAbs are first selected for their ability to specifically recognize one or more NK cell receptors, such as KIR2DL1, KIR2DL2, KIR2DL3, KIR2DL5A, KIR2DL5B, KIR3DL1, KIR3DL2, KIR3DL3, KIR2DS1, KIR2DS2, KIR2DS3, KIR2DS4, KIR2DS5, KIR3DS1, CD94, NKG2A, NKG2C, NKG2D, NKG2E, NKG2F, NKp30, NKp44, NKp46, etc. Positive monoclonal antibodies are further screened for their ability to specifically bind to NK cells taken from patients with an immunoproliferative disorder (e.g. NK-LDGL, rheumatoid arthritis, etc).

Example 2

Purification of Peripheral Blood Lymphocytes (PBL) and Generation of Polyclonal or Clonal NK Cell Populations Peripheral blood lymphocytes (PBL) are derived from NK-LDGL patients or patients with another immunoproliferative disorder, or healthy donors by Ficoll-Hipaque gradients and depletion of plastic-adherent cells. In order to obtain enriched NK cells, PBLs are incubated with anti-CD3 (JT3A), anti-CD4 (HP2.6) and anti-HLA-DR (D1.12) mAbs (30 min at 4 degrees C.) followed by goat anti-mouse coated Dynabeads (Dynal, Oslo, Norway) (30 min at 4 degrees C.) and immunomagnetic depletion (Pende et al. (1998) Eur. J. Immunol. 28:2384-2394; Sivori et al. (1997) J. Exp. Med. 186: 1129-1136; Vitale et al. (1998) J. Exp. Med. 187:2065-2072). $CD3^-4^-DR^-$ cells are used in cytolytic assays or cultured on irradiated feeder cells in the presence of 100 U/ml rIL-2 (Proleukin, Chiron Corp., Emeryville, USA) and 1.5 ng/ml PHA (Gibco Ltd, Paisley, Scotland) in order to obtain polyclonal NK cell populations or, after limiting dilution), NK cell clones (Moretta (1985) Eur. J. Immunol. 151:148-155).

Example 3

Flow Cytofluorimetric Analysis

Patient and control cells are stained with mAbs specific to a variety of NK cell receptors either that are either directly labeled or followed by PE- or FITC-conjugated isotype-specific goat anti-mouse second reagent (Southern Biotechnology Associated, Birmingham, Ala.). Samples are analyzed by one- or two-color cytofluorimetric analysis (FACScan Becton Dickinson & Co, Mountain View, Calif.) (see, e.g. Moretta et al. (1990) J. Exp. Med. 171:695-714).

Example 4

Biacore Analysis of Antibody-Substrate Interactions

Production and Purification of Recombinant Proteins

The recombinant proteins are produced in *E. coli*. cDNA encoding the entire extracellular domain of an NK cell receptor, amplified by PCR using standard methods. The nucleic acid sequences are cloned into the pML1 expression vector in frame with a sequence encoding a biotinylation signal (Saulquin et al, 2003). Protein expression is performed in the BL21(DE3) bacterial strain (Invitrogen). Transfected bacteria are grown to $OD_{600}=0.6$ at 37° C. in medium supplemented with ampicillin (100 µg/ml) and expression induced with 1 mM IPTG. Proteins are recovered from inclusion bodies under denaturing conditions (8 M urea). Refolding of the recombinant proteins is performed in 20 mM Tris, pH 7.8, NaCl 150 mM buffer containing L-arginine (400 mM, Sigma) and β-mercaptoethanol (1 mM), at room temperature, by decreasing the urea concentration in a six step dialysis (4, 3, 2, 1 0.5 and 0 M urea, respectively). Reduced and oxidized glutathione (5 mM and 0.5 mM respectively, Sigma) are added during the 0.5 and 0 M urea dialysis steps. Finally, the proteins are dialyzed extensively against 10 mM Tris, pH 7.5, NaCl 150 mM buffer. Soluble, refolded proteins are concentrated and then purified on a Superdex 200 size-exclusion column (Pharmacia; AKTA system). Surface plasmon resonance measurements are performed on a Biacore apparatus (Biacore). In all Biacore experiments HBS buffer supplemented with 0.05% surfactant P20 served as running buffer.

Protein Immobilization.

Recombinant substrate proteins produced as described above are immobilized covalently to carboxyl groups in the dextran layer on a Sensor Chip CM5 (Biacore). The sensor chip surface is activated with EDC/NHS (N-ethyl-N'-(3-dimethylaminopropyl)carbodiimidehydrochloride and N-hydroxysuccinimide, Biacore). Proteins, in coupling buffer (10 mM acetate, pH 4.5) were injected. Deactivation of the remaining activated groups was performed using 100 mM ethanolamine pH 8 (Biacore).

Affinity Measurements.

For kinetic measurements, various concentrations of the soluble antibody ($1\times10^{-7}$ to $4\times10^{-10}$ M) are applied onto the immobilized substrate ample. Measurements are performed at a 20 μl/min continuous flow rate. For each cycle, the surface of the sensor chip is regenerated by 5 μl injection of 10 mM NaOH pH 11. The BIAlogue Kinetics Evaluation program (BIAevaluation 3.1, Biacore) is used for data analysis. The soluble analyte (40 μl at various concentrations) is injected at a flow rate of 20 μl/min in HBS buffer, on dextran layers containing, e.g., 500 reflectance units (RU), and 1000 RU, of substrate.

Example 5

Figure 1B:
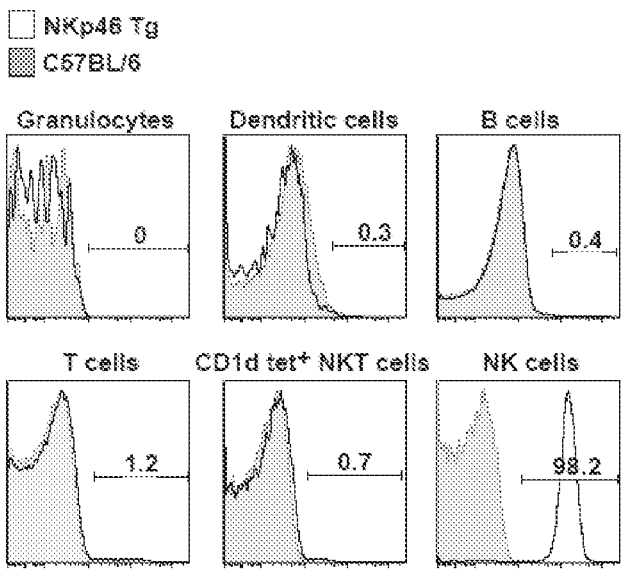
Figure 1C:
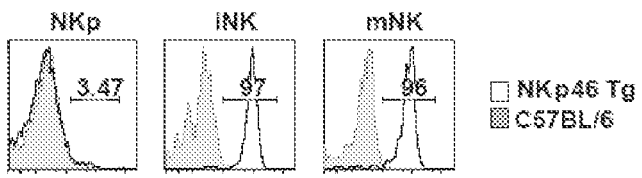
Figure 1D:
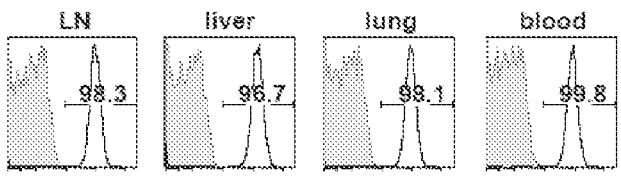
Figure 1E:
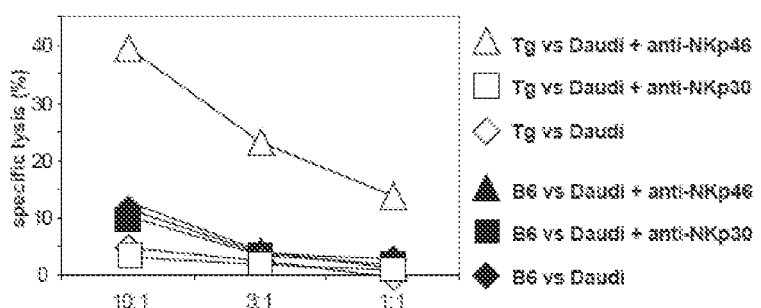

In Vivo Model for Depletion of Murine NK Cells Expressing a Human NK Cell Receptor The dissection of NK cell biological functions has been complicated by the lack of selective deficiency models. In order to investigate whether antibodies, particularly naked antibodies could be used to deplete NK cells in vivo, a model of selective deficiency was used to assess the extent to which antibodies could eliminate NK cells in a mouse. NKp46 has been shown to be a specific NK cell marker; for this reason NKp46 regulatory sequences were used to create such models. To validate the feasibility of this strategy, a transgenic vector consisting of a 24 kb human genomic region located between the NKP46 adjacent genes FCAR and NALP7 was generated (FIG. 1a). From a transgenic founder (referred to as huNKp46 Tg), offsprings were obtained at Mendelian frequencies, developed normally and were fertile. BAB281 (anti-human NKp46) antibodies that do not cross-react with mouse NKp46 were used to assess the cell surface expression of human NKp46 in these mice. Human NKp46 was not expressed on granulocytes, dendritic cells, B cells, T cells and CD1d-α-gal-cer tetramer+ NKT cells but expressed at a high and uniform level on all NK cells (FIG. 1b). Moreover, human NKp46 starts to be expressed at the immature stage of NK cell development in the bone marrow (FIG. 1c) and remains subsequently expressed at the same level by all NK cells isolated from all organs tested (FIG. 1d). Remarkably, the pattern of human NKp46 expression in huNKp46 Tg mice was thus similar to that of endogenous mouse NKp46 molecules in parental mice. Therefore, the cell surface expression of human NKp46 defined NK cells in huNKp46 Tg mice, demonstrating that human NKp46 regulatory sequences can be used to drive NK-specific gene expression. NK cells in huNKp46 Tg mice exhibited normal counts, phenotype and effector function. Importantly, redirected lysis was induced through human NKp46 (FIG. 1e), indicating that human NKp46 molecules are functional in mouse NK cells.

Example 6

In Vivo Depletion of Mouse NK Cells Using Anti-Human NKp46

Figure 2A:
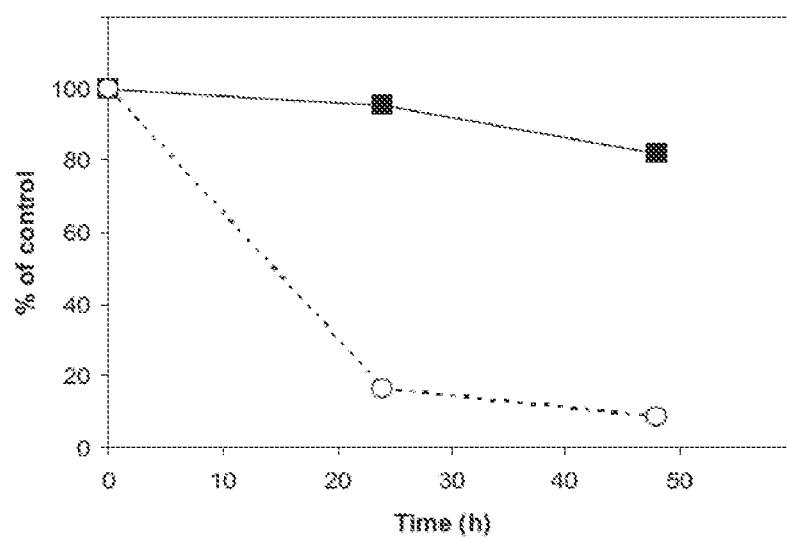
FIG. 2. NK cells from huNKp46-transgenic mice can be specifically depleted by injection of anti-human NKp46 antibodies. Groups of hu-NKp46 transgenic mice were injected i.v. with PBS (control) or a combination of three mAbs against human NKp46 as described in the methods. (a) The percentage of NK1.1+CD3− cells in the blood was measured over time after the injection. (b) 48 h after the injections, mice were sacrificed and the percentage of NK cells, TCRγδ+ T cells and CD1d-restricted NKT cells was measured in the spleen, peripheral blood, liver and lungs. Results in are expressed as the percentage of indicated cell subsets upon injection as compared to control mice.
Figure 2B:
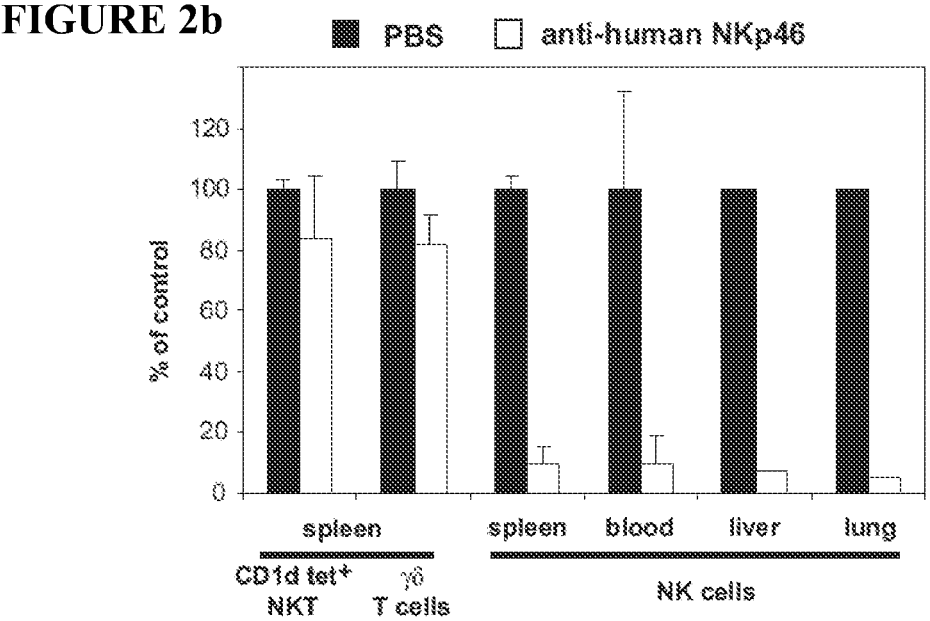

HuNKp46 Tg mice: mice were injected retro-orbitally with PBS or a mixture of three different antibodies against NKp46: BAB281 (IgG1, 100 μg), KL247 (IgM, 100 μg), and 195314 (IgG2b, R&D systems, 50 μg). I.v. administration of antihuman NKp46 antibodies led to a nearly complete disappearance of NK cells from blood and all organs tested, 2 days post-injection (FIG. 2). By contrast, NKT cell and TCR γδ+ T cell counts were not significantly affected (FIG. 2), indicating that huNKp46. Tg mice can be used as a mouse model of NK cell-selective depletion and that antibodies with Fcgamma receptor (e.g. CD16) binding ability (e.g. mouse IgG1 and IgG2b) can mediate depletion of NK cells. Using corresponding human effector regions which bind CD16 (e.g. IgG1, IgG3, or other Fc regions such as IgG2 or IgG4 modified so as to bind CD16) can therefore be used for the depletion of NK cells, notably also in bone marrow and organs, an important feature in immunoproliferative disorders where unwanted NK cells may be located in a given organ or tissue.

Example 7

Z270 Depletion of NKG2A and -C Expressing Lymphocytes Reduces the Secretion of Pro-Inflammatory Cytokines Introduction IL-15 is known to be upregulated in inflammatory sites and is known to have immunostimulatory effect on lymphocytes such as T- and NK-cells, and on monocyte derived cell-lineages. CD94/NKG2A and -C are HLA-E specific receptors that are present in high frequencies on T- and NK-cells in inflammatory sites in chronic inflammation, e.g. in rheumatoid arthritis. In these indications, the pro-inflammatory cytokine TNF-α is an important driver of inflammation, and TNF-α targeting therapies (e.g. Infliximab or Humira) can reduce inflammation. TNF-α is produced by macrophages, NK-cells, T- and B-cells. In several experiments a cell-to-cell contact-dependent mechanism between NK or T cells on one hand and monocytic derived cells such as macrophages on the other, has been shown to induce a strong production of TNF-α. We demonstrate herein that depleting CD94/NKG2A and -C positive NK and T cells with monoclonal antibodies can have an anti-inflammatory effect. This is exemplified in an in vitro assay in which we show that lymphocytes depleted for CD94/NKG2A and -C expressing cells induce less TNF-α production by a monocytic cell line, than do lymphocytes from which CD94/NKG2A and -C expressing cells have not been depleted.

Depletion of CD94/NKG2A and -C Expressing Lymphocytes Reduces the Capacity of Lymphocytes to Activate Monocytes The anti-inflammatory effects of depleting CD94/NKG2A and -C positive cells from the blood was demonstrated in vitro. For this, peripheral blood mononuclear cells (PBMC's) were isolated from fresh blood derived from healthy donors, using Heparin-containing CPT vacutainer tubes (BD Sciences), essentially according to the manufacturer's protocol. Lymphocytes were separated from monocytes by culturing the PBMC's for one hour in a Petri dish in 10 ml Glutamax containing RPMI 1640 medium, supplemented with 10% FCS and Penicillin/Streptomycin (designated medium below), to let monocytes adhere to the dish. Lymphocytes were washed once. The lymphocytes in the supernatant were subsequently incubated at 37° C., 5% $CO_2$ for ~24 hours in medium the presence of human IL-15 (BD Sciences, 50 ng/ml) in 6 well plates using a total volume of 5 ml. CD94/NKG2A and -C positive cells were removed by MACS (Miltenyi Biotech) essentially according to the manufacturer's protocol. In short, cells were washed once in sterile PBS containing 0.5% BSA. Half of the cells were incubated with a combination of anti-NKG2A (Z199) (BD Biocienses) (2 μg/ml) and anti-NKG2C (clone 134522)

Figure 3:
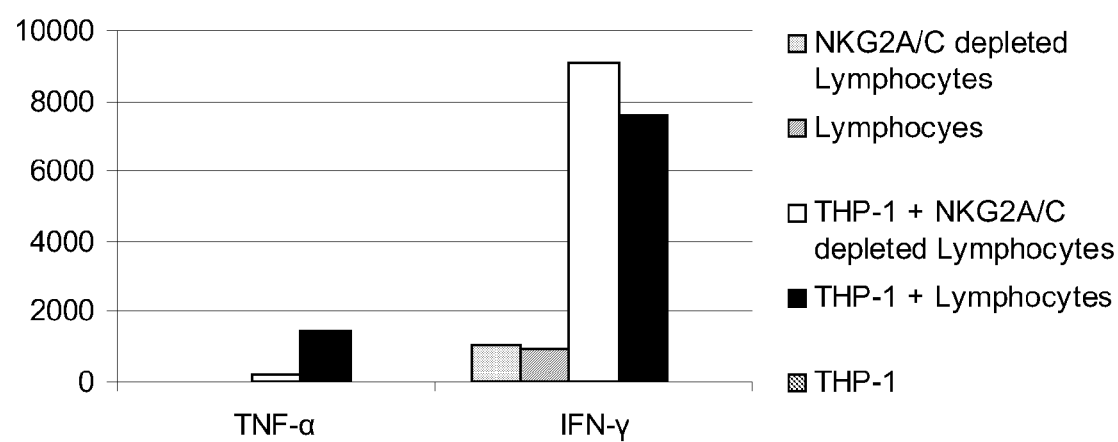
FIG. 3. Lymphocytes depleted for CD94/NKG2A and -C expressing cells (white bars) induce less TNF-alpha production when cultured with THP-1 cells, than lymphocytes that contain CD94/NKG2A and -C expressing cells (black bars). No TNF-alpha production was observed when lymphocytes or THP-1 cells were cultured alone (see legends). In contrast, IFN-alpha production was not affected, indicating that lymphocytes were activated when co-cultured with THP-1 cells.

(R&D systems) (2.5 µg/ml), for 30 minutes on ice. Cells were subsequently washed twice in sterile PBS/0.5% PBS and incubated with 20 µl goat anti-mouse IgG MicroBeads to 80 µl cells on ice for 30 minutes. Then cells were washed with PBS/0.5% BSA. CD94/NKG2A and -C positive cells were removed using an LD MACS column. The removal of CD94/NKG2A and -C positive cells was typically >95%, as assessed by analyzing anti-CD94 (HP-3D9) (Pharmingen) stained cells in flowcytometry (FACSarray) (see FIG. 3). Flow-through cells were washed once in Glutamax containing RPMI 1640 medium, supplemented with 10% FCS and Penicillin/Streptomycine RPMI 1640 (Gibco) and cultured in 24 well plates with THP-1 cells for 24 hours in a lymphocyte-to-THP-1 ratio of 10:1, using a volume of 1 ml medium/well. The activation of THP-1 cells by CD94/NKG2A- and -C-depleted lymphocytes was analyzed by measuring the secretion of TNF-α, IFN-γ, IL-2, -4, -6, and -10 in the tissue-culture medium on FACSarray (BD Biosciences), using the CBA Th1/Th2 cytokine kit II kit, essentially according to the manufacturer's protocol. A marked reduction of TNF-α production was observed in cultures where NKG2A and -C depleted lymphocytes were used compared to non-depleted cells. Thus, depleting CD94/NKG2A and -C expressing lymphocytes reduces the pro-inflammatory capacity of lymphocytes.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A method of treating a patient with ulcerative colitis, Crohn's disease, psoriasis, or spondyloarthropathy, comprising:
administering to said patient a therapeutically effective amount of one or more antibodies that each specifically binds to a receptor selected from KIR2DL1, KIR2DS1, KIR2DL2, KIR2DL3, KIR2DS4, and KIR3DL2 expressed on a T cell and/or a NK cell, wherein the one or more antibodies each comprises an $F_c$ region of the human IgG1 or human IgG3 isotype capable of binding to CD16.

2. The method of claim 1, wherein said antibody does not comprise an element selected from the group consisting of a radioactive isotope, toxic peptide, and toxic small molecule.

3. The method according to claim 1, wherein said receptor is KIR3DL2.

4. A method for reducing inflammation in a patient with ulcerative colitis, Crohn's disease, psoriasis, or spondyloarthropathy, comprising administering to said patient a composition comprising a therapeutically effective amount of an antibody that specifically binds to a receptor selected from KIR2DL1, KIR2DS1, KIR2DL2, KIR2DL3, KIR2DS4, and KIR3DL2 expressed on a T cell and/or a NK cell, wherein the antibody comprises an $F_c$ region of the human IgG1 or human IgG3 isotype capable of binding to CD16.

5. The method according to claim 4, wherein said antibody specifically binds to KIR3DL2.

6. The method of claim 4, wherein said antibody does not comprise an element selected from the group consisting of a radioactive isotope, toxic peptide, and toxic small molecule.

* * * * *

UNITED STATES PATENT AND TRADEMARK OFFICE
CERTIFICATE OF CORRECTION

PATENT NO. : 9,447,185 B2  
APPLICATION NO. : 12/089314  
DATED : September 20, 2016  
INVENTOR(S) : Romagne et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 970 days.

Signed and Sealed this  
Twenty-ninth Day of August, 2017

Joseph Matal  
*Performing the Functions and Duties of the*  
*Under Secretary of Commerce for Intellectual Property and*  
*Director of the United States Patent and Trademark Office*